(12) United States Patent
Segeritz et al.

(10) Patent No.: US 12,370,222 B2
(45) Date of Patent: Jul. 29, 2025

(54) COMPOSITIONS AND METHODS FOR OBTAINING ORGANOIDS

(71) Applicant: STEMCELL TECHNOLOGIES CANADA INC., Vancouver (CA)

(72) Inventors: Charis-Patricia Segeritz, Vancouver (CA); Ryan Conder, Vancouver (CA); Michael Riedel, Vancouver (CA)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 0 days.

(21) Appl. No.: 18/679,906

(22) Filed: May 31, 2024

(65) Prior Publication Data

US 2024/0316114 A1    Sep. 26, 2024

Related U.S. Application Data

(62) Division of application No. 16/618,148, filed as application No. PCT/CA2018/050625 on May 29, 2018, now Pat. No. 12,029,764.

(60) Provisional application No. 62/512,138, filed on May 29, 2017.

(51) Int. Cl.
| | |
|---|---|
| *A61K 35/38* | (2015.01) |
| *A61L 27/36* | (2006.01) |
| *A61L 27/38* | (2006.01) |
| *A61L 27/54* | (2006.01) |
| *G01N 33/48* | (2006.01) |

(52) U.S. Cl.
CPC .......... *A61K 35/38* (2013.01); *A61L 27/3633* (2013.01); *A61L 27/3813* (2013.01); *A61L 27/54* (2013.01); *A61L 2300/434* (2013.01); *A61L 2430/28* (2013.01); *G01N 33/48* (2013.01)

(58) Field of Classification Search
None
See application file for complete search history.

(56) References Cited

U.S. PATENT DOCUMENTS 12,029,764 B2 *   7/2024   Segeritz .............. A61L 27/3633
2012/0196312 A1   8/2012   Sato et al.

FOREIGN PATENT DOCUMENTS

WO   WO-2017037295 A1 *   3/2017   ......... A61L 27/3834

OTHER PUBLICATIONS

Asai, A. et al., "Paracrine signals regulate human liver organoid maturation from induced pluripotent stem cells", Development (2017) 144, 1056-1064 doi:10.1242/dev.142794.

* cited by examiner

*Primary Examiner* — Blaine Lankford
(74) *Attorney, Agent, or Firm* — Smart & Biggar LP

(57) ABSTRACT

A method for obtaining epithelial organoids is provided. In one embodiment, the method comprises culturing one or more epithelial ducts, epithelial duct fragments and/or epithelial stem cells isolated therefrom in contact with an extracellular matrix in the presence of a basal medium, wherein the medium is free of FGF and/or nicotinamide. Organoids obtained by the methods described herein, and uses thereof, are also provided.

18 Claims, 20 Drawing Sheets

COMPOSITIONS AND METHODS FOR OBTAINING ORGANOIDS

CROSS REFERENCE TO RELATED APPLICATIONS

This application is a divisional of U.S. application Ser. No. 16/618,148, which is a national phase entry of PCT/CA2018/050625 filed May 29, 2018 (which designates the U.S.), which claims priority from U.S. provisional application No. 62/512,138, filed May 29, 2017, the contents of which are incorporated herein by reference in their entirety.

FIELD

The present disclosure relates to cell culture methods, and to cell culture media formulations for use in said cell culture methods. More particularly, this disclosure relates to cell culture methods and cell culture media for culturing primary tissues or the cells thereof, and the maintenance, expansion, differentiation and self-organization of the foregoing into epithelial three dimensional (3D) structures.

BACKGROUND

Since the discovery of adult stem and progenitor cells, the scientific community has been focused on defining the molecular cues required to support the propagation and differentiation of such cells ex vivo. The derivation of adult stem cells avoids ethical concerns associated with the utilization of embryonic stem cells. Stem cells are commonly cultured and differentiated under 2D culture systems. Unfortunately, these 2D cultures of stem cells have many shortcomings when utilized as in vitro representatives of the endogenous tissues. For example, 2D cultures are limited in their ability to generate cellular polarization, acquire cellular functionality and recapitulate human physiology in vitro. This decreases their accuracy as cellular models for pharmaceutical drug screenings and for therapeutic developments. Thus, there is a need for improved culture systems of stem cells and their derivative cell types that more accurately reproduce the in vivo tissue of interest.

The design of artificial extracellular matrices based on naturally-occurring adhesion proteins, such as collagen, laminin, entactin, fibronectin and vitronectin, have supported the direction of research towards culture systems in a 3D environment. Such natural and artificial extracellular matrices strive to mimic the cellular in vivo niche.

Organoids are 3D in vitro models of in vivo biological materials and processes and serve as a novel platform to address diverse research questions pertinent to embryonic development, tissue regeneration and tissue functionality, drug toxicity and drug sensitivity, disease modelling, and adult stem cell biology. Epithelial organoids are obtained through isolation and expansion of stem and progenitor cells from an organ's stem cell niche and comprise an epithelial mono- or multilayer of stem/progenitor cells and differentiated cells that preserve key physiological features of the organ from which they are derived. Epithelial organoids are reliant on an in vitro system that closely mimics an in vivo environment. Once established, epithelial organoids are enabling scientists to investigate their specific research questions in a physiologically-relevant context.

There is an interest to develop cell culture methods for deriving organoids representative of certain tissues. While some epithelial organs contain senescent and quiescent tissue, other epithelial tissues comprise an epithelium characterized by continuous turnover rates under homeostasis and faster rates when exposed to an injury stimulus. Accordingly, such tissues lend themselves particularly well to the derivation of organoids.

The intestinal epithelium was one of the first organoid systems established. However, there has been increasing interest to also develop cell culture methods for deriving organoids from other tissues. Examples of these tissues include the liver and pancreas. Similar to the intestinal epithelium, the liver possesses high regenerative potential, especially under conditions of acute or chronic injury. Different cell types, including oval cells, hepatic progenitors, and mature hepatocytes have been attributed to the renewal and turnover of hepatic tissue during homeostasis and damage. Facultative stem cells localized to the Canals of Hering and bile ductules have also been implicated as a source of self-renewing cell types in these functions. The culture and propagation of such cells ex vivo is favourable over primary hepatocytes which are finite and limited in their proliferative capacity and functionality once isolated from the liver.

Recently, single cells expressing either the adult stem cell marker Lgr5 or Epcam have been isolated from damaged and undamaged mouse liver tissue and were shown to be competent to give rise to hepatic organoids in vitro that mimic the endogenous in vivo hepatic, epithelial architecture when cultured in Expansion Medium (Huch et al., 2013, Nature, 494(7436): 247-50; Huch et al. 2015, Cell, 160(1-2): 299-312). The methods outlined in the associated patent application (US 20130189327) may be improved upon in a number of ways. First, toxin-mediated experimental liver injury, as described in US 20130189327, may be challenged by animal welfare standards. Second, even if injured liver tissue may be accessed, it may be desirable to avoid the burdensome and technically challenging tasks of isolating hepatic ducts through manual picking. Third, the expansion medium disclosed in US 20130189327 is complex and expensive, thus it may be desirable to titrate and/or remove of numerous components including various growth factors, small molecules, vitamins, and chemicals. Fourth, as US 20130189327 requires an undefined, conditioned medium that is technically challenging to prepare, the use of an unconditioned medium may offer certain benefits.

Therefore there is a need for simplified cell culture media and methods for generating epithelial organoids. There is a further need for cell culture media which may support higher expansion rates of the epithelial organoids. Most importantly, there is a need for a method to improve the yield of epithelial ducts and epithelial duct fragments from epithelium-lined organs allowing for the formation of organoids in a cell culture medium providing the benefits described above. There is a further need to establish media and protocols that may be used across various epithelial organs towards the establishment of organ-specific organoids.

SUMMARY

The inventors have developed a method capable of isolating large quantities of cells from uninjured epithelial tissues that may be expanded and cultured long-term under minimal culture conditions and may be suitable for downstream differentiation toward matured cell types.

The present disclosure comprises methods for obtaining an organoid derived from one or more cells isolated from an epithelial tissue, wherein the methods comprise culturing the one or more cells in a culture medium of the disclosure.

In one embodiment, the method for obtaining high yields of expandable cells comprises the enzymatic digestion of epithelial tissue into epithelial ducts and/or epithelial duct fragments, optionally frequent mechanical disruption of the digesting tissue, and optionally subsequent filtering of the digested tissue through a cell strainer to eliminate single cells (rather than manual picking of ducts under the microscope). The yielding epithelial ducts and/or epithelial duct fragments may be cultured in a medium of the disclosure.

In another embodiment, the method for obtaining high yields of expandable cells comprises the enzymatic digestion of epithelial tissue into single epithelial stem and/or progenitor cells, optionally frequent mechanical disruption of the digesting tissue, and optionally subsequent filtering of the digested tissue through a cell strainer to separate larger debris from single epithelial stem and/or progenitor cells. The yielding cells may be cultured in a medium of the disclosure.

Optionally, the epithelial ducts and/or epithelial duct fragments and/or the epithelial stem and/or progenitor cells may also be supported by mixture of a culture medium of the disclosure with an extracellular matrix.

In one embodiment, the epithelial ducts and/or epithelial duct fragments, and/or epithelial stem and/or progenitor cells may be seeded in a basal medium. Such basal medium may be characterized by an absence of one, some or all of EGF, a R-spondin, a fibroblast growth factor and Nicotinamide.

In another embodiment, the basal expansion medium comprises an activator of the Wnt—beta-catenin pathway.

In another embodiment, the expansion medium comprises an Epidermal Growth Factor (EGF) and an activator of the Wnt—beta-catenin pathway.

In another embodiment, the expansion medium comprises a Noggin protein or a different antagonist of Bone Morphogenic Protein (BMP), an inhibitor of signaling downstream of BMP such as LDN 193189, an EGF and an activator of the Wnt—beta-catenin pathway.

Accordingly, the disclosure provides a method for obtaining an epithelial organoid, the method comprising culturing one or more epithelial ducts, epithelial duct fragments and/or epithelial stem or progenitor cells isolated therefrom in the presence of a basal medium, wherein the medium is free of FGF and/or nicotinamide.

In one embodiment, the medium comprises a Wnt agonist, optionally CHIR99021 and/or a Wnt agonist selected from one or more of Wnt, Wnt3a, Norrin, R-Spondin 1, R-Spondin 2, R-Spondin 3, R-Spondin 4 and a GSK inhibitor.

In one embodiment, the medium comprises EGF. In another embodiment, the medium comprises a B27 component and/or a N2 component, and/or N-Acetylcysteine.

In another embodiment, the epithelial stem or progenitor cells are human cells, mouse cells, rat cells, hepatic epithelial stem cells, pancreatic epithelial stem cells or intestinal epithelial stem cells.

In another embodiment, the medium is effective for long-term culture of the epithelial organoid, wherein the long-term culture is about 50 or more passages.

In another embodiment, the method further comprises culturing the one or more epithelial ducts, epithelial duct fragments and/or epithelial stem or progenitor cells in contact with an extracellular matrix.

In another embodiment, the method further comprises culturing the one or more epithelial ducts, epithelial duct fragments and/or epithelial stem or progenitor cells in contact with reduced support from an extracellular matrix.

In one embodiment, the extracellular matrix concentration ranges between 0.1 to 50% (v/v).

In another embodiment, the method further comprises culturing the epithelial stem or progenitor cells from the epithelial duct and/or epithelial duct fragment in suspension. In one embodiment, the extracellular matrix concentration is about 0.1% (v/v) or less.

In another embodiment, the extracellular matrix comprises Matrigel™.

In another embodiment, the epithelial ducts, epithelial duct fragments and/or epithelial stem or progenitor cells isolated therefrom are obtained from uninjured tissue.

In another embodiment, the method further comprises subjecting the epithelial organoid to maturation and/or differentiation conditions.

The disclosure also provides a liver organoid, wherein the liver organoid is obtained according to the methods disclosed herein.

The disclosure also provides a pancreatic organoid, wherein the pancreatic organoid is obtained according to the methods disclosed herein.

The disclosure also provides an intestine organoid, wherein the intestine organoid is obtained according to the methods disclosed herein.

The disclosure also provides a method of conducting a drug discovery screen; assaying toxicity; researching embryology, cell lineages, and differentiation pathways; studying gene expression including recombinant gene expression; researching mechanisms involved in injury and repair; researching inflammatory and infectious diseases; studying pathogenic mechanisms of cell transformation and etiology of cancer comprising obtaining an epithelial organoid according to the methods disclosed herein.

The disclosure further provides a method of treating a liver disorder, condition, or disease or for regenerative medicine in a subject, comprising administering a liver organoid as disclosed herein to a subject in need thereof.

The disclosure further provides a method of treating a pancreas disorder, condition, or disease or for regenerative medicine in a subject, comprising administering a pancreas organoid as disclosed herein to a subject in need thereof.

The disclosure further provides a method of treating an intestine disorder, condition, or disease or for regenerative medicine in a subject, comprising administering an intestine organoid as disclosed herein to a subject in need thereof.

The disclosure also provides a method for obtaining an epithelial organoid, the method comprising:
 isolating an organ comprising epithelial tissue or a portion thereof;
 cutting and disrupting mechanically the isolated organ or the portion thereof to yield one or more pieces of epithelial tissue;
 digesting enzymatically the one or more pieces of epithelial tissue to yield epithelial ducts and/or duct fragments;
 collecting the digested epithelial ducts and/or duct fragments through a cell strainer;
 plating the collected epithelial ducts and/or duct fragments; and
 culturing the plated epithelial ducts and/or duct fragments in the presence of a basal medium, wherein the medium is free of FGF and/or nicotinamide.

In one embodiment, the medium comprises a Wnt agonist, optionally CHIR99021 or a Wnt agonist is selected from one or more of Wnt, Wnt3a, Norrin, R-Spondin 1, R-Spondin 2, R-Spondin 3, R-Spondin 4 and a GSK inhibitor.

In one embodiment, the medium comprises EGF.

In another embodiment, the medium comprises a B27 component and/or a N2 component and/or N-Acetylcysteine.

In another embodiment, the method further comprises maintaining intactness of a ductal architecture during digestion.

In another embodiment, the method further comprises treating a surface or implement with a surfactant prior to contact with the one or more pieces of epithelial tissue.

In another embodiment, the method further comprises plating the collected epithelial ducts and/or epithelial duct fragments in contact with an extracellular matrix.

In another embodiment, the method further comprises plating the collected epithelial ducts and/or epithelial duct fragments in contact with reduced support from an extracellular matrix.

In another embodiment, the extracellular matrix concentration ranges between 0.1 to 50% (v/v).

In another embodiment, the method further comprises plating the collected epithelial ducts and/or epithelial duct fragments in suspension.

In another embodiment, the extracellular matrix concentration is about 0.1% (v/v) or less.

In another embodiment, the extracellular matrix comprises Matrigel™.

In another embodiment, the method further comprises subjecting the epithelial organoid to maturation and/or differentiation conditions.

The disclosure also provides a medium for obtaining an epithelial organoid, the medium comprising a basal medium free from a FGF and/or nicotinamide.

In one embodiment, the medium further comprises a Wnt agonist, optionally CHIR99021.

In another embodiment, the Wnt agonist is selected from one or more of Wnt, Wnt3a, Norrin, R-Spondin 1, R-Spondin 2, R-Spondin 3, R-Spondin 4 and a GSK inhibitor.

In another embodiment, the medium further comprises an EGF.

In another embodiment, the medium further comprises a B27 component and/or a N2 component and/or N-Acetylcysteine.

In another embodiment, the medium further comprises an extracellular matrix.

In one embodiment, the concentration of the extracellular matrix ranges between 0.1 to 50% (v/v).

In another embodiment, the concentration of the extracellular matrix is about 0.1% (v/v) or less.

In another embodiment, the extracellular matrix comprises Matrigel™.

The disclosure also provides a culture medium comprising a basal medium, HEPES, sodium bicarbonate, Rh insulin, progesterone, putrescine, sodium selenite, human apo-transferrin, corticosterone, D-(+)-Galactose, and BSA.

In one embodiment, the medium further comprises R-Spondin-1 and/or CHIR99021.

In another embodiment, the medium further comprises EGF.

In another embodiment, the medium further comprises a BMP antagonist.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

The disclosure describes media and methods for culturing epithelial organoids. The disclosure also describes media and methods for forming epithelial organoids. The epithelial organoids of this disclosure may be derived from one or more epithelial organs, or portions thereof, epithelial tissue, epithelial ducts, epithelial duct fragments, and/or epithelial stem/progenitor cells in accordance with the methods disclosed herein and in the presence of a medium disclosed herein.

The disclosed media and methods allow for initiation and maintenance of epithelial organoids, including but not limited to organoids derived from hepatic, pancreatic, pulmonary, and intestinal tissue. The epithelial organoids may be derived from human or animal tissues.

Cell Culture Media

In one aspect, the present disclosure provides culture media for deriving and/or obtaining epithelial organoids. The epithelial organoids may be derived and/or obtained in accordance with the methods described herein below.

In one embodiment, the epithelial organoids are obtained by culturing one or more epithelial ducts, epithelial duct fragments and/or epithelial stem cells isolated therefrom in the presence of a culture medium described below.

In one embodiment, the culture medium (also referred to here as "medium" or "expansion medium") for forming and/or culturing epithelial organoids is a basal medium. As used herein, the term "basal medium" refers to a medium that contains the elements required for the growth of animal or human cells, namely a carbon source, water, salt, and a source of amino acids and nitrogen (for example, bovine or yeast extract). Exemplary basal media include, but are not limited to, Dulbecco's Modified Eagle Medium (DMEM), DMEM/Nutrient Mixture F-12 (DMEM/F-12), Advanced DMEM/F-12, RPMI 1640, Iscove's Modified Dulbecco's Medium (IMDM), Minimum Essential Medium (MEM) and/or Basal Medium Eagle (BME). In one embodiment, the basal medium comprises a combination of the above exemplary basal media at various ratios.

Figure 1:
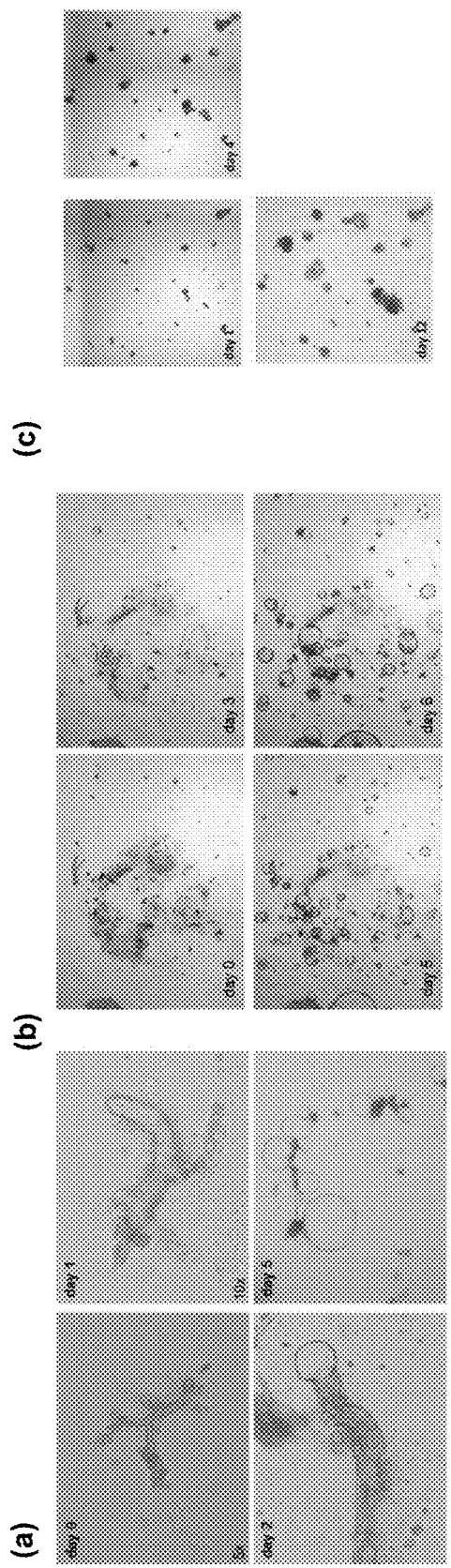
FIG. 1 shows expansion of isolated epithelial tissue from murine liver, pancreas and intestine into (a) hepatic organoids, (b) pancreatic organoids, and (c) intestinal organoids respectively.
Figure 2:
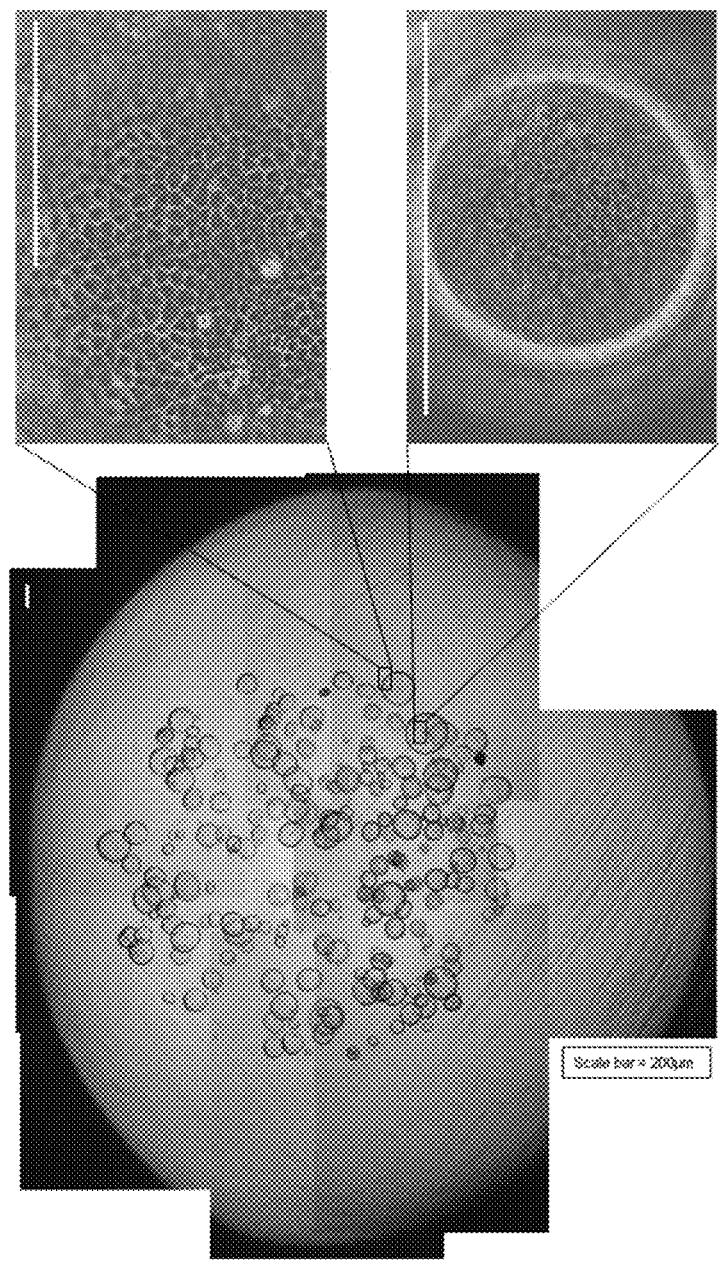
FIG. 2 shows epithelial organoids exhibiting a single epithelium, hollow lumen, and exhibiting characteristic cell-cell junctions and morphologies.

The present inventors have shown that epithelial organoids can be obtained by culturing one or more epithelial ducts, epithelial duct fragments and/or epithelial stem or progenitor cells isolated therefrom in medium lacking a FGF and/or nicotinamide. The one or more epithelial ducts, epithelial duct fragments and/or epithelial stem or progenitor cells cultured in a medium of this disclosure have been shown to yield organoids capable of undergoing an initial expansion (FIG. 1). Such organoids may exhibit an epithelial cell layer, a hollow lumen, and typical cell-cell junctions and morphologies (FIG. 2).

Accordingly, in one embodiment, the medium is free from, or devoid of a FGF and/or a derivative or agonist thereof. As used herein, the term "FGF" or "fibroblast growth factor" refers a member of fibroblast growth factor family of signaling molecules. The FGF may be a natural or synthetic FGF. In one embodiment, the FGF is recombinant FGF. For example, 22 FGFs are known in humans. In another embodiment, the medium is free from, or devoid of, nicotinamide and/or a derivative or agonist thereof. In another embodiment the medium is free from a FGF (and/or a derivative or agonist thereof) and/or nicotinamide (and/or a derivative or agonist thereof). In another embodiment, the medium is free from, or devoid of a FGF and nicotinamide, and/or derivatives or agonists thereof. In yet another embodiment, the medium has an undetectable amount of a FGF and/or nicotinamide, or has no exogenously added FGF and/or nicotinamide.

In one embodiment, the medium is an unsupplemented medium. In another embodiment, the medium is a medium supplemented with amino acids, vitamins, organic/inorganic salts, sugars and/or antioxidants.

In another embodiment, the medium is supplemented with L-glutamine. L-glutamine is an essential amino acid that is unstable at physiological pH in a liquid medium. L-glutamine for supplementing cell culture media is commercially available. In one embodiment, the medium is supplemented with 0.5 mM to 10 mM glutamine, or 1 mM to 5 mM glutamine, or 2 mM to 4 mM glutamine. In certain embodiments, the L-glutamine is a stabilized form of L-glutamine. An example of a stabilized form of L-glutamine is L-Alanyl-L-glutamine.

The medium may also comprise a buffering agent for maintaining an appropriate pH of the medium. In one embodiment, the buffering agent is HEPES. Optionally, the medium comprises up to 25 mM HEPES, about 20 mM HEPES, about 15 mM HEPES, about 10 mM HEPES, about 5 mM HEPES, about 1 mM HEPES, or less. In another embodiment, the buffering agent is sodium bicarbonate. As a guideline, sodium bicarbonate may be provided in medium at approximately 1.0 g/L to 5.0 g/L per 4-10% $CO_2$ in the cell culture conditions. In one embodiment, the medium is supplemented with about 1.5 g/L sodium bicarbonate for cells grown in 5% $CO_2$, or at about 2 g/L for cells grown in 5% $CO_2$, or at about 3 g/L for cells grown in 5% $CO_2$, or at about 4 g/L for cells grown in 5% $CO_2$. In another embodiment, the basal medium is supplemented with more than one buffering agent, for example both HEPES and sodium bicarbonate. In a particular such embodiment, the basal medium comprises less than about 25 mM HEPES and less than about 5 g/L sodium bicarbonate.

In another embodiment, the medium comprises at least one B-27 and/or N2 supplement. Such supplements and the components thereof are well known in the field of mammalian cell culture. B-27 and N2 are commercially available from a variety of suppliers. In another embodiment, medium comprises one or more subcomponents of B-27 and/or N2. In a specific embodiment, the medium comprises one or more of the following B-27 and/or N2 subcomponents: Rh insulin; progesterone; putrescine; sodium selenite; human apo-transferrin; corticosterone; D-(+)-Galactose; and BSA. In addition, if the medium comprises certain of the B-27 and/or N2 subcomponents, it may be desirable to deviate from the working concentrations of complete B-27 and N2. For example, in a specific embodiment, the medium comprises B-27 and/or N2 subcomponents at lower concentrations. In one embodiment of the medium, the B-27 and/or N2 subcomponents may be used within the following final concentration ranges: 0.01-100 µg/mL Rh insulin; 2 nM to 400 UM progesterone; 0.1-10 mM putrescine; 1 ng/ml to 100 µg/mL sodium selenite; 0.2-200 µg/mL human apo-transferrin; 1-500 ng/ml corticosterone; 30 µM to 30 mM D-(+)-Galactose; and 0.5 µg/mL to 5 mg/mL BSA.

In one embodiment, the medium comprises DMEM/F-12 or Advanced DMEM/F-12 and: 10-20 mM HEPES, 0.5 to 1.5 g/L sodium bicarbonate, 55-75 µg/mL Rh insulin, 35-45 nM progesterone, 0.1 to 0.8 mM putrescine, 5-15 ng/ml sodium selenite, 60-100 µg/mL human apo-transferrin, 10-30 ng/ml corticosterone, 10-20 µg/mL D-(+)-Galactose, and 1-4 mg/mL BSA. In another embodiment, the medium comprises, consists of, or consists essentially of DMEM/F-12 or Advanced DMEM/F-12 and about: 15 mM HEPES, 1.2 g/L sodium bicarbonate, 62 µg/mL Rh insulin, 38 nM progesterone, 0.4 mM putrescine, 10 ng/mL sodium selenite, 80 µg/mL human apo-transferrin, 20 ng/ml corticosterone, 15 µg/mL D-(+)-Galactose, and 2.6 mg/mL BSA. This medium is referred to herein as "Medium A".

In one embodiment, epithelial organoids formed in the presence of Medium A are cultured about 5 or more passages. For example, hepatic organoids formed in accordance with the methods described herein and in the presence of Medium A may undergo an initial expansion into organoids.

In other embodiments, the culture medium for obtaining epithelial organoids comprises a basal medium as described above, such as Medium A, and further comprises at least one, at least two, at least three or at least four activators of the Wnt—beta-catenin pathway. As used herein, the term "activator of the Wnt—beta-catenin pathway" refers to any molecule, antibody, compound or genetic modifier (e.g. siRNA) leading to any beta-catenin- and/or YAP/TAZ-induced transcriptional changes. For example, the at least one, or the more than one, activator of the Wnt—beta-catenin pathway may be any molecule or compound that positively regulates signaling of a Frizzled family receptor. Non-limiting examples of molecules or compounds positively regulating signaling of a Frizzled family receptor include a Wnt protein or agonist; and/or Norrin protein or agonist; and/or an R-Spondin protein or R-spondin agonist that binds to Lgr4/5 and RNF43/ZNRF3.

In one embodiment, the at least one, at least two, at least three or at least four, activators of the Wnt—beta-catenin pathway is or comprises a molecule or compound that sequesters a negative regulator of the Wnt—beta-catenin pathway. Non-limiting examples of molecules or compounds sequestering a negative regulator of the Wnt—beta-catenin pathway include, but are not limited to, SB-216763, CHIR99021, and CAS 853220-52-7.

In another embodiment, the molecule or compound that sequesters a negative regulator of the Wnt-beta-catenin pathway is a small molecule inhibitor. In a particular embodiment, the small molecule inhibitor is an inhibitor of GSK-3. For example, the inhibitor of GSK-3 may be CHIR99021. In a particular embodiment, CHIR99021 is present at a concentration ranging between 1 µM to 10 µM, or ranging between 3 uM to 8 uM, or ranging 4 um to 7 uM, or ranging between 5 uM to 6 uM.

In one embodiment, the Wnt protein is Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 or Wnt16. In another embodiment, the Wnt protein is Wnt3a. Wnt3a may be a recombinant protein or added as conditioned medium. In another embodiment, Wnt3a may be supplemented to the medium alongside molecules and compounds that stabilize the protein, for example its post-translational modification configuration, strengthening its signaling capacity.

In another embodiment, the R-Spondin protein or agonist is R-Spondin-1, R-Spondin-2, R-Spondin-3, or R-Spondin-4. In a particular embodiment, the R-Spondin protein or agonist is recombinant. The R-Spondin protein or agonist of the culture media may be present at a concentration ranging between about 0.1 ng/ml to 1 mg/mL, or about 1 ng/ml to 1 µg/mL, or about 3 ng/ml to 150 ng/mL or about 5 ng/ml to 100 ng/ml or about 10 ng/ml to 50 ng/ml. In a particular embodiment, the R-Spondin is R-Spondin-1.

In one embodiment, the medium comprises more than one activator of the Wnt—beta-catenin pathway. In another embodiment, the medium comprises R-Spondin 1 and CHIR99021.

In another embodiment, the Norrin protein or agonist is an orthologue of invertebrate burs and pburs genes. In another embodiment, the Norrin protein or agonist acts as cognate ligand for LGR4, Fzl4, LGR5 and LGR6. In another embodiment, the Norrin protein or agonist inhibits signaling through a BMP. In a particular embodiment, the Norrin protein or agonist is recombinant. In another embodiment, the Norrin protein or agonist of the culture media is present at a concentration ranging between about 0.1 ng/mL to 1 mg/mL, or about 1 ng/ml to 1 µg/mL, or about 3 ng/ml to 150 ng/ml or about 5 ng/ml to 100 ng/ml, or about 10 ng/mL to 50 ng/mL.

In one embodiment, the medium comprises Advanced DMEM/F-12 or DMEM/F-12, and: 10-20 mM HEPES, 0.5 to 1.5 g/L sodium bicarbonate, 0.005-0.025 µg/mL R-Spondin-1 and/or 2.5-4.5 µM CHIR99021, 55-75 µg/mL Rh insulin, 35-45 nM progesterone, 0.1 to 0.8 mM putrescine, 5-15 ng/ml sodium selenite, 60-100 µg/mL human apo-transferrin, 10-30 ng/ml corticosterone, 10-20 µg/mL D-(+)-Galactose, and 1-4 mg/mL BSA. In another embodiment, the medium comprises, consists of, or consists essentially of Advanced DMEM/F-12 or DMEM/F-12, and about: 15 mM HEPES, 1.2 g/L sodium bicarbonate, 0.015 µg/mL R-Spondin-1 and/or 3.75 µM CHIR99021, 62 µg/mL Rh insulin, 38 nM progesterone, 0.4 mM putrescine, 10 ng/ml sodium selenite, 80 µg/mL human apo-transferrin, 20 ng/ml corticosterone, 15 µg/mL D-(+)-Galactose, and 2.6 mg/mL BSA. This medium is referred to herein as "Medium B".

In one embodiment, epithelial organoids formed in the presence of Medium B are cultured about 10 or more passages. For example, hepatic organoids formed in accordance with the methods described herein and in the presence of Medium B may undergo an initial expansion, and the culture thereof may be supported for at least 10 passages. Overall, Medium B may be used for the formation and culture of epithelial organoids.

In other embodiments, culture media for forming and/or culturing epithelial organoids comprises a basal medium as described above (for example, Medium A). In another embodiment, the medium further comprises at least one activator of the Wnt—beta-catenin pathway as described above (for example, Medium B). In another embodiment, the medium further comprises one or multiple members of the Epidermal growth factor (EGF) family, such as EGF, TGF-alpha, amphiregulin, betacellulin, epiregulin, heparin-binding EGF-like growth factor, epigen and neuregulin-1, -2, -3 and -4.

In a particular embodiment, the EGF family member is present at a concentration ranging between about 0.1 ng/ml to 1 mg/mL, or about 1 ng/ml to 1 µg/mL, or about 3 ng/ml to 150 ng/ml or about 5 ng/mL to 100 ng/ml, or about 10 ng/ml to 50 ng/ml.

In one embodiment, the medium comprises Advanced DMEM/F-12 or DMEM/F-12, and: 10-20 mM HEPES, 0.5 to 1.5 g/L sodium bicarbonate, 0.005-0.025 µg/mL R-Spondin-1 and/or 2.5-4.5 µM CHIR99021, 0.01-1.0 g/mL EGF, 55-75 µg/mL Rh insulin, 35-45 nM progesterone, 0.1 to 0.8 mM putrescine, 5-15 ng/ml sodium selenite, 60-100 µg/mL human apo-transferrin, 10-30 ng/ml corticosterone, 10-20 µg/mL D-(+)-Galactose, and 1-4 mg/mL BSA. In another embodiment, the medium comprises, consists of, or consists essentially of Advanced DMEM/F-12 or DMEM/F-12, and about: 15 mM HEPES, 1.2 g/L sodium bicarbonate, 0.015 µg/mL R-Spondin-1 and/or 3.75 µM CHIR99021, 0.05 µg/mL EGF, 62 µg/mL Rh insulin, 38 nM progesterone, 0.4 mM putrescine, 10 ng/ml sodium selenite, 80 µg/mL human apo-transferrin, 20 ng/ml corticosterone, 15 µg/mL D-(+)-Galactose, and 2.6 mg/mL BSA. This medium is referred to herein as "Medium C".

In one embodiment, epithelial organoids formed in the presence of Medium C are cultured for about 40 or more passages. For example, hepatic organoids formed in accordance with the methods described herein and in the presence of Medium C may undergo an initial expansion, and the culture thereof may be supported for about 40 or more passages. Overall, Medium C may be used for the formation and culture of epithelial organoids and for the longer term culture of epithelial organoids.

In other embodiments, culture media for obtaining epithelial organoids comprises a basal medium as described above (for example, Medium A). The medium may also comprise at least one or more than one activator of the Wnt—beta-catenin pathway as described above (for example, Medium B) and one or multiple members of the EGF family as described above (for example, Medium C). In another embodiment, the medium further comprises one or more inhibitors or antagonists of BMP or BMP signaling.

In one embodiment, the one or more inhibitor or antagonist of a BMP is a protein such as, by way of non-limiting example, noggin, chordin, follistatin, sclerostin, CTGF/CCN2, gremlin, Cerberus, DAN, PRDC, decorin, alpha-2 macroglobulin proteins, and derivatives thereof.

In a particular embodiment, the concentration of the protein for inhibiting a BMP, such as Noggin, is present at a concentration ranging between about 0.1 ng/ml to 1 mg/mL, or about 1 ng/ml to 1 µg/mL, or about 3 ng/mL to 150 ng/ml or about 5 ng/mL to 100 ng/ml, or about 10 ng/mL to 50 ng/ml.

In another embodiment, the one or more inhibitor or antagonist of BMP signaling is a protein as indicated above and/or a small molecule inhibitor such as, by way of non-limiting example, LDN 193189 or Dorsomorphin, which may inhibit signaling downstream of BMP.

In embodiments where one or more inhibitor or antagonist of BMP or BMP signaling may be used to supplement culture media, such inhibitor may be present at a concentration ranging between 0.001 nM to 10 mM, optionally 0.0001 µM to 0.2 µM. In the particular embodiment where culture media is supplemented with LDN 193189, it may be present at a concentration between 0.001 nM to 10 mM, optionally 0.001 µM and 1 µM.

In one embodiment, the medium comprises Advanced DMEM/F-12 or DMEM/F-12, and: 10-20 mM HEPES, 0.5 to 1.5 g/L sodium bicarbonate, 0.005-0.025 µg/mL R-Spondin-1 and/or 2.5-10 µM CHIR99021, 0.01-1.0 µg/mL EGF, 0.0.05-0.30 µg/mL Noggin, 0.05-0.15 µM LDN, 55-75 µg/mL Rh insulin, 35-45 nM progesterone, 0.1 to 0.8 mM putrescine, 5-15 ng/ml sodium selenite, 60-100 µg/mL human apo-transferrin, 10-30 ng/ml corticosterone, 10-20 µg/mL D-(+)-Galactose, and 1-4 mg/mL BSA.

In another embodiment, the medium comprises, consists of, or consists essentially of Advanced DMEM/F-12 or DMEM/F-12, and about: 15 mM HEPES, 1.2 g/L sodium bicarbonate, 0.015 µg/mL R-Spondin-1 and/or 7.5 µM CHIR99021, 0.05 µg/mL EGF, 0.015 µg/mL Noggin, 0.1 µM LDN, 62 µg/mL Rh insulin, 38 nM progesterone, 0.4 mM putrescine, 10 ng/ml sodium selenite, 80 µg/mL human apo-transferrin, 20 ng/mL corticosterone, 15 µg/mL D-(+)-Galactose, and 2.6 mg/mL BSA. This medium is referred to herein as "Medium D".

In one embodiment, epithelial organoids formed in the presence of Medium D are cultured for about 50 or more passages and support splitting ratios of approximately 1:30. For example, hepatic organoids formed in accordance with the methods described herein and in the presence of Medium D may undergo an initial expansion, and the culture thereof may be supported for about 50 or more passages. Overall, Medium D may be used for the formation and culture of epithelial organoids and for the longer term culture of epithelial organoids.

In still other embodiments, the medium described herein (including, but not limited to, Medium A, Medium B, Medium C, and/or Medium D) is further supplemented with other compounds or molecules that support the culture of human or animal cells. For example, in one embodiment, the medium is supplemented with N-acetyl-L-cysteine. In a particular embodiment, N-acetyl-L-cysteine is present at a concentration ranging between 750 µM to 1500 µM.

In a further embodiment, the medium is supplemented with a hepatocyte growth factor (HGF). In a particular embodiment, HGF is present at a concentration ranging between about 0.1 ng/ml to 1 mg/mL, or about 1 ng/ml to 1 µg/mL, or about 5 ng/ml to 150 ng/ml or about 10 ng/ml to 100 ng/mL. In a different embodiment the medium lacks HGF.

In yet a further embodiment, the medium is supplemented with Gastrin. In a particular embodiment, Gastrin is present at a concentration ranging between 0.001 µM to 0.2 µM. In a different embodiment the medium lacks Gastrin.

The media described herein (for example, but not limited to, Medium A, Medium B, Medium C, and Medium D) may also be combined with 0.1-100% (v/v) Matrigel™, or other extracellular matrices or combinations of extracellular matrix components (ie. laminins, collagens, proteoglycans, non-proteoglycan polysaccharides, fibronectin, vitronectin, elastin), prior to plating organoids.

The media of this disclosure, for example, but not limited to, Medium A, Medium B, Medium C, and Medium D, may be supplemented with some, none, or all of the foregoing additional supplements at concentrations appropriate for the particular application. Furthermore, any of the supplements described herein, if not specifically reciting a small molecule analogue, may be substituted with a small molecule analog of the corresponding protein at concentrations appropriate for the particular application.

Any of the foregoing supplements added to the medium described herein may be prepared as 2-1000× stock solutions and stored at −20° C. Frozen stock solution may be thawed and added to the disclosed culture media as appropriate. Complete media may be stored at 4° C. for approximately 1-3 months.

Methods

The disclosure provides methods for obtaining epithelial organoids. The methods comprise culturing one or more epithelial ducts, epithelial duct fragments and/or epithelial stem cells isolated therefrom in contact with an extracellular matrix and in the presence of a medium. In one embodiment, the medium is a basal medium which, as described above, is free of a FGF and/or nicotinamide, or includes a FGF and/or nicotinamide at undetectable levels, or is free of an exogenously added FGF and/or nicotinamide.

The surfaces, cavities and tubes of animal organs, glands, and blood vessels are lined with epithelial tissues. The epithelium comprises a tightly-packed sheet of cells that are generally polarized into opposing apical and basal membranes. One function of the epithelium is to guard the interface between the two different environments. Epithelial tissues can contain stem cell niches that replenish differentiated somatic cell types during regular tissue maintenance and at enhanced rates during injury responses.

In particular, the ductal microanatomy of the epithelium is commonly home to the organ's stem cell niche and includes stem/progenitor cells that are known to have clonogenic potential (Sato et al., 2009, *Nature*; Huch et al., 2013 *Nature*). Accordingly, epithelial stem/progenitor cells (also referred to herein as "epithelial stem cells") are a good substrate for generating epithelial organoids under appropriate culturing conditions.

As used here, the term "organoid" refers to a three dimensional in vitro model of an organ. An organoid can provide a realistic micro-anatomy of the organ from which it is derived. Accordingly, the term "epithelial organoid" refers to an organoid obtained from one or more epithelial stem/progenitor cells. The epithelial stem/progenitor cell(s) may be from any organ, including but not limited to, the liver, lung, pancreas or intestine. An organoid obtained from one or more liver epithelial stem/progenitor cells is also referred to herein as a "liver organoid", an organoid obtained from one or more pancreatic epithelial stem/progenitor cells is also referred to herein as a "pancreatic organoid", and an organoid obtained from one or more intestinal epithelial stem/progenitor cells is also referred to herein as an "intestinal organoid".

In one embodiment, an epithelial organoid is established from single epithelial stem/progenitor cells. Optionally, the single epithelial stem/progenitor cells may be isolated through fluorescence-activated cell sorting of digested epithelial tissue. However, efficiencies of establishing organoids may be increased if the epithelial stem/progenitor cells are plated as epithelial fragments. As used herein, the term "epithelial fragment" refers to a fragment, or portion, of epithelial tissue. An epithelial fragment may be obtained through partial enzymatic or mechanical breakdown of the epithelial tissue. Without being bound by theory, epithelial stem/progenitor cells integrated within epithelial fragments may likely still be embedded in their in vivo stem cell niche and may benefit from paracrine signaling during the initiation of organoid cultures.

In one embodiment, the epithelial fragment is an epithelial duct or a fragment thereof. As used herein, the term "epithelial duct" refers to a bodily passage or tube lined with epithelial cells and conveying a secretion or other substance.

As described above, epithelial ducts contain stem/progenitor cells (Sato et al., 2009, *Nature*; Huch et al., 2013 *Nature*).

Organs comprising epithelia, or portions thereof, may be isolated from a subject using any method known to the person skilled in the art of tissue dissection. For example, an organ may be removed from a freshly deceased subject using conventional dissection. Alternatively, a portion of an organ may be obtained from a subject by way of a biopsy. Notwithstanding the method used to isolate the organ or portion thereof, subsequent processing of the organ or portion thereof may be timely commenced. The subject may be a human or an animal, such as a rodent.

Isolated organs, or portions thereof, and the derivatives thereof—such as epithelial tissues, epithelial ducts, epithelial duct fragments, or epithelial cells—or established organoids themselves may be adhesive and may tend to adhere to surfaces or implements used to process the epithelial organs or portions thereof, such as plastic ware and/or pipettes or pipette tips. At any stage of the disclosed methods, it may be desirable to rinse the surfaces or implements in contact with isolated epithelia or derivatives thereof, or established organoids with a surfactant. Use of a surfactant, such as AggreWell™ Rinsing Solution, helps prevent adherence of the foregoing to the surfaces or implements. After rinsing the surfaces or implements with the surfactant, it may be further desirable to wash the rinsed surface or implement with a basal medium, such as Advanced DMEM/F-12 or DMEM/F-12.

Figure 3:
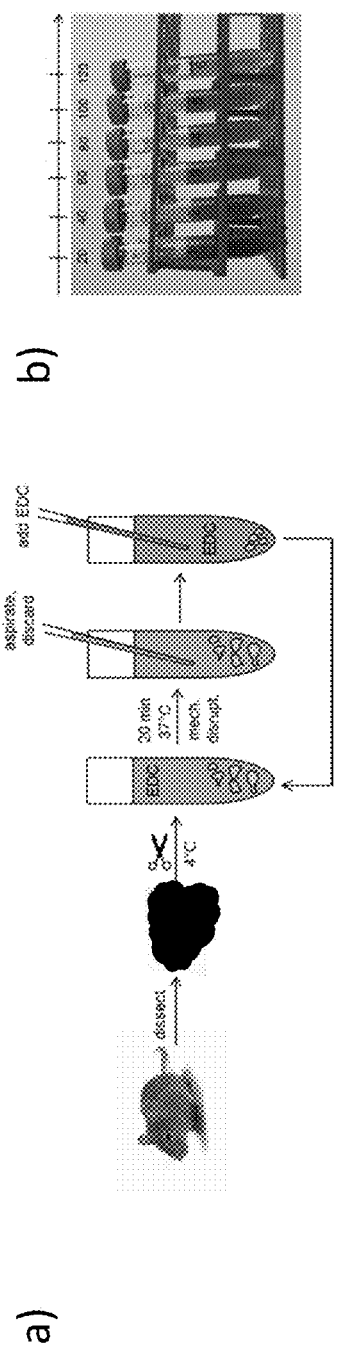
FIG. 3 shows processing of epithelial organs. (a) Generalized protocol for processing an organ comprising epithelia to yield epithelial ducts, epithelial duct fragments, and/or epithelial stem cells contained in the epithelial ducts and/or epithelial duct fragments. EDC=enzymatic digestion cocktail. (b) A time-course in minutes showing progressively less turbidity of the buffer comprising digestive enzyme(s) in sequentially digested samples.

A generalized protocol as described below is depicted in FIG. 3. Additional details of a method for culturing primary tissue or the cells thereof, and the maintenance, expansion, differentiation and self-organization of the foregoing into epithelial 3D structures may be described in relevant part herein, or be known to the person skilled in the art.

To obtain fragments from an epithelial tissue, a fresh organ or portion thereof may be cut into smaller pieces of tissue. The fresh organ or portion thereof may be cut using any appropriate implement such as a blade or an edge, whether or not in combination with a pair of tweezers or the like. The tissue of the organ, or portion thereof, may be cut into a size appropriate for downstream processing. For example, suitably-sized tissue may correspond to a volume of approximately 1-5 mm$^3$ or approximately 2-4 mm$^3$ or approximately 3 mm$^3$.

While processing the organ, or portion thereof, into epithelial tissue, both the organ, or portion thereof, and the epithelial tissue may be bathed in ice-cold solution. The ice-cold solution may be a buffer, such as a phosphate buffered saline, or a standard tissue culture medium such as Advanced DMEM/F-12 or DMEM/F-12. The ice-cold solution may be any solution that keeps the organ, or portion thereof, and the epithelial tissue cold and viable for downstream processing.

An ice-cold solution containing epithelial tissue may be transferred to a container, where the epithelial fragments may settle to the bottom thereof. Once most or substantially all of the tissue have settled to the bottom of the container, the ice-cold solution may be removed. The pellet of epithelial tissue may be promptly submerged in an appropriate volume of buffer comprising digestive enzyme(s). In one embodiment, the buffer comprising digestive enzymes may be an Enzyme Digestion Cocktail. In a particular embodiment, the Enzyme Digestion Cocktail may comprise Dispase and/or Collagenase. Where the Enzyme Digestion Cocktail comprises Collagenase, the Collagenase may be Collagenase type XI, or Collagenase type IV, or any other Collagenase that may digest epithelial tissue. In a further embodiment, the Enzymatic Digestion Cocktail may be supplemented with 1% Fetal Bovine Serum. In another embodiment, the Enzymatic Digestion Cocktail may be supplemented with DNAse I, at a concentration of about 0.1 µg/mL to 100 µg/mL, or about 1 µg/mL to about 50 µg/mL, or about 5 µg/mL to 20 µg/mL. The concentration of digestive enzymes may vary depending on the type(s) of enzyme used. For example, the concentration may be 0.0001 to 10% (w/v).

The tube containing the epithelial tissue and the buffer comprising digestive enzyme(s) may be placed for a sufficient period of time in conditions under which the digestive enzymes may function. For example, certain digestive enzymes work optimally at a temperature around 37° C., such as between 20° C. and 40° C. Any environment that may sustain temperatures at which the digestive enzymes function may be desirable. For example, the tube containing the epithelial tissue and the buffer comprising digestive enzyme(s) may be placed in a heated water bath or a heated oven until the epithelial tissue is sufficiently digested. The digestion may occur under static conditions or in motion, e.g. through rotation or shaking of the tissue. The incubation time may depend on such factors as, but not limited to, the complexity and size of the epithelial tissue and the volume of the digestive enzyme buffer. For example, a collection of ~3 mm$^3$ epithelial tissues may require an initial incubation time of 5 to 60 minutes, 10 to 50 minutes, 20 to 40 minutes, or approximately 10, 20, 30, 40 or 50 minutes.

After incubating the epithelial tissue for a time sufficient for the digestion thereof, the solution comprising the digested epithelial tissue may be vigorously agitated. Any method of vigorous agitation may be used, provided that the digested epithelial tissue is not irreparably damaged and rendered ineffective for downstream applications. For example, the solution comprising the digested epithelial tissue may be pipetted up- and down a sufficient number of times. As another example, the solution comprising the digested epithelial tissue may be vigorously mixed, such as by a vortex.

Following sufficient vigorous agitation of the digested epithelial tissue contained in the buffer comprising digestive enzyme(s), the agitated, undigested epithelial tissue may settle to the bottom of the container. The buffer comprising digestive enzyme(s) may be removed away from the agitated, semi-digested epithelial tissue, as further described below.

The removed solution comprising digestive enzyme(s) may further comprise suspended, digested epithelial ducts, epithelial duct fragments and single cells, which may or may not be visible in the buffer comprising digestive enzyme(s). It may be necessary to repeat the foregoing digestion cycle multiple times until all or substantially all of the epithelial tissue has been digested and broken down to yield epithelial ducts. The removed solution comprising particulate matter suspended therein may therefore be pooled and stored on ice while the remaining epithelial tissue pellet may be subjected to further digestion cycles with intermitted, mechanical disruption of the digested tissue and collection of the supernatant. While continuing to harvest and pool the digestive enzyme supernatant, the digestion cycles may be repeated until no more traces of undigested tissue remains.

The repetition of the digestion cycle may be necessary depending on such factors as, but not limited to, the complexity and volume of the epithelial tissue, the volume of buffer comprising digestive enzyme(s), concentration and composition of the digestive enzyme(s), the duration of incubation in the buffer comprising digestive enzyme(s), or the temperature of incubation in the buffer comprising digestive enzyme(s). In certain embodiments, it may take up to 5 or more digestion cycles of approximately, 10, 20, 30, 40, or 50 minutes to sufficiently digest epithelial tissue into epithelial ducts and/or epithelial duct fragments. In another embodiment, in lieu of several digestion cycles, a single prolonged digestion may be chosen as well. FIG. 3b depicts the progressively lighter-in-appearance supernatant of the buffer comprising digestive enzyme(s) and digested material after successive digestion cycles.

It may be desirable to obtain a solution comprising only epithelial ducts and/or epithelial duct fragments in the supernatant, or a supernatant comprising substantially only epithelial ducts and/or epithelial duct fragments. The appearance of epithelial ducts and/or epithelial duct fragments will be known to the person skilled in the art of processing epithelial tissues. For example, some characteristics of epithelial ducts and/or epithelial duct fragments may include a whitish colour, which do not readily settle by gravity in an aqueous solution and may therefore be captured and pooled in the spent enzymatic supernatant during the aforementioned digestion cycles. Smaller epithelial duct fragments are oftentimes not visible with the naked eye.

Figure 4:
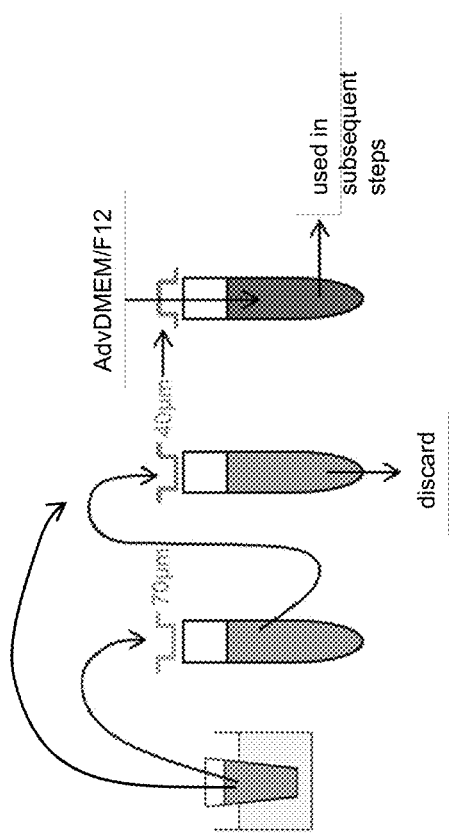
FIG. 4 shows filtering epithelial ducts and/or epithelial duct fragments, showing an optional first, pre-clearing step to filter out larger debris.

To isolate and enrich for epithelial ducts and/or epithelial duct fragments from the buffer comprising digestive enzyme(s), this solution may be passed through a filter having a sufficient mesh size (FIG. 4). The size of intact epithelial ducts may typically be on the order of approximately 70 µm and larger. The size of epithelial duct fragments may typically be on the order of 37-70 µm. Accordingly, in certain embodiments it may be sufficient to provide a filter having a mesh size of approximately 30 µm to 80 µm to remove only single cells, but capture all epithelial ducts and/or epithelial duct fragments. In another embodiment, it may be desirable to pass the epithelial ducts and/or epithelial duct fragments in the buffer comprising digestive enzyme(s) over a 40 µm filter. In a further embodiment, it may be desirable to pre-clear larger debris from the buffer comprising digestive enzyme(s) by passing this solution over a filter having a relatively larger mesh size. For example, a filter having a mesh size of about 70-80 µm may be used for this purpose. Notwithstanding, the mesh size of the filter used for the pre-clearing step should be of an appropriate size to allow all epithelial ducts and/or epithelial duct fragments to pass through, while retaining larger debris such as undigested epithelial tissue. In this particular embodiment, the flow-through devoid of larger debris may subsequently be passed through a second, smaller mesh size filter (i.e. approximately 40 µm) to capture the ductal fragments in the filtrant as indicated above.

The filtrant or pre-cleared filtrant may be collected from the filter surface. Any method of removing the filtrate or pre-cleared filtrate away from the filter surface is contemplated by this disclosure. In an exemplary method of removing the filtrant or pre-cleared filtrant away from the filter surface, the filter surface may be reversed or inverted and the contents thereon may be collected in an appropriate container by placing the reversed or inverted filter surface over the container and rinsing the other side of the filter surface with an appropriate solution. An appropriate solution may include a buffer such as a phosphate buffered saline, or another solution such as a basal medium or cell culture medium. The collected filtrant or pre-cleared filtrant should settle to the bottom of the container, and the solution removed away from the pellet comprising the filtrant or pre-cleared filtrant. It may be necessary to subject the container and its contents to a centrifugal force sufficient to pellet the filtrant or pre-cleared filtrant, but not otherwise damage the filtrant or pre-cleared filtrant so as to render it ineffective for downstream applications. In one embodiment, the filtrant and pre-cleared filtrant may be centrifuged at approximately 300×g for approximately 5 minutes.

Figure 5:
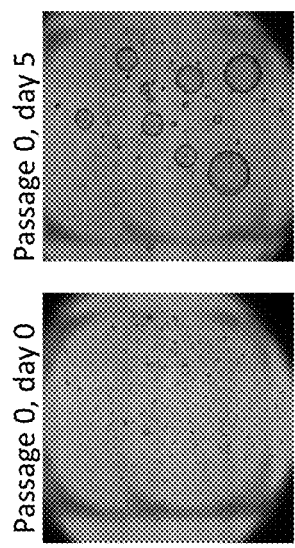
FIG. 5 shows sub-confluently plated epithelial ducts and/or epithelial duct fragments.

Once the pellet of epithelial ducts and/or epithelial duct fragments has settled to the bottom of the container and it has been separated away from the supernatant, the pellet of epithelial ducts and/or epithelial duct fragments, or a portion thereof, may be plated in a culture vessel. The culture vessel may be any culture vessel for culturing cells. For example, the culture vessel may be a Petri dish, culture flask, or a 6-, 12-, 24-, 48-, or 96-well format culture plate. The number/density of epithelial ducts and/or epithelial duct fragments plated in the culture vessel may depend on the particular type of culture vessel used. In an embodiment where the epithelial ducts and/or epithelial duct fragments are plated in a 24-well plate, it may be desirable to split the epithelial ducts and duct fragments of one mouse epithelial organ, for example, into 3-10 wells. The skilled person will understand that the number of epithelial ducts and/or epithelial duct fragments harvested per organ may be varied, but in certain embodiments the epithelial ducts and/or epithelial duct fragments may be plated at such density that the epithelial ducts and/or epithelial fragments do not merge during subsequent culturing. FIG. 5 depicts an exemplary sub-confluent density of plated fragments or single cells.

It may be desirable to suspend the epithelial ducts and/or epithelial duct fragments in an extracellular matrix prior to plating. As used herein, the term "extracellular matrix" refers to a collection of extracellular molecules that provide structural and biochemical support to surrounding cells. Both natural and synthetic extracellular matrices are contemplated within the present disclosure. In one embodiment, the matrix comprises extracellular matrix proteins. Examples of extracellular matrix proteins include, but are not limited to, laminin, collagen, fibronectin, vitronectin, and entactin. Various matrices comprising extracellular matrix proteins are commercially available, such as Matrigel™.

In one embodiment, the pellet of epithelial ducts and/or epithelial duct fragments from one mouse liver may be combined with approximately 100 µL of extracellular matrix (for example, Matrigel™) and 5-100 µL, or 10-90 µL, or 20-80 µL, or 30-70 µL, or 40-60 µL of the suspension may be plated in the center of a well of a 24-well culture plate. In another embodiment, more than one extracellular matrix dome comprising epithelial ducts and epithelial duct fragments (prepared as above) may be plated in a single well. The skilled person may appreciate that any number of extracellular matrix domes consisting of any volume of extracellular matrix may be plated in a culture vessel, provided that each extracellular matrix dome is distinct, or substantially distinct.

In another embodiment, epithelial ducts and/or epithelial fragments may be put in contact with a mixture of culture media, as disclosed herein, and an extracellular matrix at ratios of approximately 1:2. However, the final concentration of extracellular matrix (for example, Matrigel™) may vary between 10-99.9% (v/v). The resulting suspension may then be plated as described above.

In yet another embodiment, epithelial ducts and/or epithelial duct fragments may be added to culture media, as disclosed herein, wherein the culture media comprises 0.1-50% (v/v) extracellular matrix, optionally 1-20% (v/v) or 5-10% (v/v) extracellular matrix, such as Matrigel™. In particular, plating a mixture of epithelial ducts and/or epithelial duct fragments and a culture medium comprising 0.1-50% (v/v) extracellular matrix, optionally 1-20% (v/v) or 5-10% (v/v) extracellular matrix in an appropriate culture vessel may permit culture of organoids with reduced support (i.e. in suspension or suspension-like conditions) of an extracellular matrix. Reduced support of an extracellular matrix provides organoids a semi-solid environment wherein a culture medium is combined with the extracellular matrix at appropriate ratios. In such embodiments, the culture vessel may be a low-adherence culture vessel, such as a low adherence 6-well plate, 12-well plate, 24-well plate or otherwise. In one embodiment, the culture medium may be first added cold to each cold well, followed by addition and the mixing in of thawed extracellular matrix. As the next step, the stem cell-containing material isolated from the organ (for example, epithelial ducts and/or epithelial duct fragments) may be added to the well. The 6-well plate containing a plated mixture of epithelial ducts and/or epithelial duct fragments and a culture medium comprising 0.1-50% (v/v) extracellular matrix may be placed on, for example, a 1.9 cm diameter orbital shaker at approximately 70 rpm and cultured at 37° C. A 12-well plate containing a plated mixture of epithelial ducts and/or epithelial duct fragments and a culture medium comprising 0.1-50% (v/v) extracellular matrix may be placed on, for example, a 1.9 cm diameter orbital shaker at approximately 80 rpm. Generally, organoids cultured with reduced support of an extracellular matrix support faster expansion rates and organoid yields in shorter time than organoids cultured in static extracellular matrix domes.

In yet another embodiment, epithelial ducts and/or epithelial duct fragments may be added to culture media, as disclosed herein, wherein the culture media comprises about 0.1% (v/v) or less extracellular matrix, such as Matrigel™. In particular, plating a mixture of epithelial ducts and/or epithelial duct fragments and a culture medium comprising about 0.1% (v/v) extracellular matrix or less in an appropriate culture vessel may permit suspension culture of organoids.

In embodiments where ≥10% (v/v) extracellular matrix is used, once the one or more extracellular matrix domes comprising epithelial ducts, epithelial duct fragments and/or epithelial stem/progenitor cells isolated therefrom have polymerized, a sufficient amount of culture medium may be added to the well. The culture medium for culturing the domes comprising epithelial ducts, epithelial duct fragments, or the epithelial stem/progenitor cells isolated therefrom or nascent therein, may be any medium as described herein, for example, Medium A, Medium B, Medium C or Medium D. A sufficient volume of culture media may be added to the culture vessel in order to cover the domes and to ensure the epithelial ducts, epithelial duct fragments, and/or the epithelial stem/progenitor cells are sufficiently nourished.

The seeding efficiency of organoid fragments may generally be close to 50%. Although organoid fragments at low densities may efficiently expand in a culture medium of this disclosure, the seeding of 200 fragments generally results in the incorporation of 100 fragments in a Matrigel™ dome. Such a fragment density may be well-suited for the expansion thereof over 5-7 days within the volume provided by a 30 µL Matrigel™ dome, for example. However, Matrigel™ domes having different volumes may also be suitable in particular applications. By way of non-limiting examples, Matrigel™ domes corresponding to volumes of 10 µL to 1 mL may be used as desired.

In embodiments where it is desired to form and expand epithelial organoids from single epithelial stem and/or progenitor cells, the filtered fraction described above comprising epithelial ducts and/or epithelial duct fragments may be exposed to a single-cell dissociation enzyme such as Accutase™, Trypsin, Gentle Cell Dissociation Reagent or TrypLE™. The enzyme may be delivered in a basal medium and the concentration and duration adapted to the amount of material exposed to the enzymes. The single cell dissociation enzyme may also be supplemented with DNAse I. Upon completing the digestion, enzymatic activity may be eliminated through the addition of FBS-containing basal medium and/or diluting out the enzyme. The single-cell digested suspension may additionally be passed through a single-cell strainer to remove any cells that have not been completely dissociated into single units. In one embodiment, the epithelial fragments may be harvested from one mouse organ and captured as the filtrant on a 40 μm filter, pelleted and digested with about 1-10 mL TrypLE™ and about 0.1 μg/mL to 100 μg/mL, or about 1 μg/mL to 50 μg/mL, or about 5 μg/mL to 20 μg/mL DNAse I for about 3-45 minutes at 37° C. The enzymatic digestion reaction may be stopped by the addition of DMEM/F-12 supplemented with 10% FBS. The cell suspension may then be filtered through a 40 μm filter, pelleted and plated as a cell-Matrigel™ mixture.

Single epithelial stem/progenitor cells prepared in this way may be plated in a dome of >10% (v/v) extracellular matrix; in suspension with reduced support of 0.1-50% (v/v) extracellular matrix; or in suspension with about 0.1% (v/v) or less extracellular matrix as described above. For example, 5,000-50,000 cells may be seeded into a dome composed of 100% (v/v) extracellular matrix or into a suspension well containing 10% (v/v) extracellular matrix.

Figure 6:
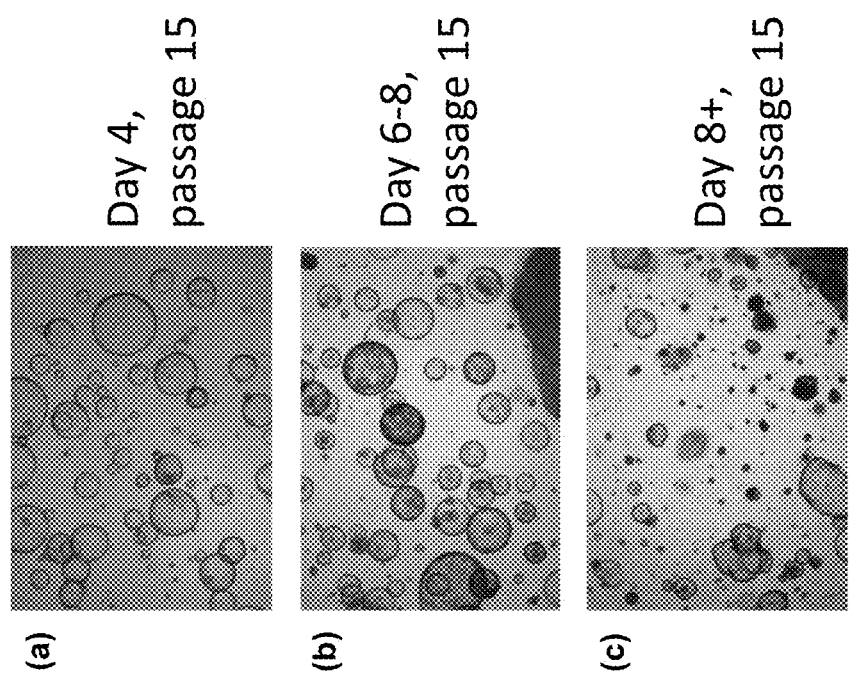
FIG. 6 shows the progressive degeneration of epithelial organoids. (a) Healthy organoids at day 4, passage 15. (b) Organoids showing signs of darkening lumen. (c) Organoids showing signs of darkened and collapsed lumen.

The expansion of organoids from the epithelial ducts and/or epithelial duct fragments, or from single epithelial stem/progenitor cells, may be monitored daily to track their growth. In general, organoids may be subcultured within a week and before their lumen turns dark and collapses (FIG. 6), preventing the organoids from forming black, dense clusters of cells. During early passages, the lumen of an organoid may darken and collapse at approximately day 4-6. During later passages, the lumen of organoid may darken and collapse at approximately day 6-7. Established organoids may be subcultured mechanically into organoid fragments or enzymatically into organoid fragments or single cells. The organoid yield may be higher if established organoids are subcultured mechanically and seeded as organoid fragments.

For mechanical splitting of dome cultures, the intactness of an extracellular matrix dome may be verified using a light microscope. If the extracellular matrix dome comprising epithelial organoids is substantially intact, the medium may be removed from the culture vessel, such as by aspiration. Using a p1000 pipette, approximately 1000 μL of a cold culture media, such as a basal culture media (i.e. Advanced DMEM/F-12), may be forcefully directed approximately toward the center of each extracellular matrix dome. A volume of the cold culture medium, may be vigorously pipetted up and down in the culture vessel approximately 5, 10, 15, 20 or 30 times to disrupt the extracellular matrix dome and organoids into fragments, but avoiding the complete disruption of organoids into single cells. A fraction of the resulting suspension may be transferred into an empty culture vessel for counting.

In an exemplary embodiment, three 10 μL volumes of the cell suspension may be plated as individual volume domes into an empty well of a 6-well plate. Using a light microscope, the number of organoid clumps in each 10 μL volume dome may be counted, and the number of organoid clumps in the cell suspension determined. Once the density of organoid clumps in the cell suspension is determined, a volume comprising approximately 200 clumps may be added to a tube holding 1 mL of a culture medium as disclosed herein, such as a basal medium, may be centrifuged at 300×g for 5 minutes. Without disturbing the pellet, the supernatant may be carefully aspirated, and the pellet may be resuspended in at least 10 μL to about 100 μL of extracellular matrix. The suspension of extracellular matrix comprising organoid clumps may be plated in one well of a pre-warmed 24-well plate and allowed to polymerize. Once the extracellular matrix dome comprising the organoid clumps has polymerized, approximately 750 μL of a pre-warmed culture medium, as disclosed herein, may be added to each dome (i.e. well). It may be preferable to add the pre-warmed culture media against the side of the well in order to not disturb the extracellular matrix dome. For well-established organoid cultures, the quantification of organoid fragment densities in a well may be omitted by subculturing organoids at suitable and constant split ratios, e.g. 1:30.

For enzymatic splitting, the intactness of an extracellular matrix dome may be verified using a light microscope. If the extracellular matrix dome comprising epithelial organoids is substantially intact, the medium may be removed from the culture vessel, such as by aspiration. Using a p1000 pipette, approximately 500 μL of a cold culture media, such as a basal culture media (i.e. Advanced DMEM/F-12), may be forcefully directed approximately toward the center of each extracellular matrix dome and allowed to sit for approximately 1 minute. Using a p1000 pipette tip, the extracellular matrix dome may be brought into solution, such as by upward and downward pipetting, and/or compaction, and the volume transferred to a fresh tube. The well in which the extracellular matrix dome was disrupted may be rinsed with an additional volume of culture media and pooled with the contents of the fresh tube.

The contents of the fresh tube may be vigorously pipetted up and down approximately 5, 10, 15, or 20 times. The vigorously pipetted solution may be centrifuged for 5 minutes at approximately 300×g, and the supernatant carefully removed and discarded. The pellet may subsequently be contacted with a suitable enzymatic solution for dissociating the organoids or portions thereof substantially into single cells and placed for a sufficient period of time in conditions under which the digestive enzyme(s) may function. For example, certain digestive enzymes work optimally at a temperature around 37° C., such as between 20° C. and 40° C. Any environment that may sustain temperature at which the digestive enzymes function may be desirable. Also, the digestion may occur under static conditions or in motion, e.g. through rotation or shaking of the tissue. For example, the tube may be placed in a heated water bath or a heated oven until the organoids or portions thereof have sufficiently dissociated. In one embodiment, incubating the organoids or portions thereof in Single Cell Dissociation Buffer for about 10 or 20 minutes in a 37° C. water bath may be sufficient to dissociate the organoids or portions thereof into single cells.

Once the organoids or portions thereof have been sufficiently exposed to the enzymatic solution, this solution may be combined with approximately 3 mL of culture medium, such as a basal media as described herein, and the cell number therein may be determined using a hemocytometer. A desired number of live cells may be transferred into a tube containing culture media, such as the basal medium described herein, and centrifuged at approximately 300×g for 5 minutes. The pellet comprising single cells may be resuspended in any appropriate volume of extracellular matrix and plated as a single or multiple domes in one well of a pre-warmed 24-well plate and allowed to polymerize. Once the extracellular matrix dome comprising the dissociated single cells has polymerized, approximately 750 μL of a pre-warmed culture media, as disclosed herein, may be added to each dome (i.e. well). It may be preferable to add pre-warmed culture media against the side of the well in order to not disturb the Matrigel™ dome.

For mechanical splitting of suspension cultures, a cell scraper may be used to release organoids and Matrigel™ and transferred to a new vessel. In one embodiment, the vessel may be a 15 mL Falcon tube. Using a p1000 pipette, approximately 1000 μL of a cold culture medium, such as a basal culture medium (i.e. Advanced DMEM/F-12), may be forcefully directed toward the bottom of the tube containing the settled organoids. A volume of the cold culture medium, may be vigorously pipetted up and down in the culture vessel approximately 5, 10, 15, 20 or 30 times to disrupt the extracellular matrix dome and organoids into fragments, but avoiding the complete disruption of organoids into single cells. A fraction of the resulting suspension may be transferred into an empty culture vessel for counting. The desired number of organoid fragments may then be transferred to a new culture plate already containing cold culture medium and extracellular matrix. The culture medium may then be returned to an orbital shaker at 37° C.

Subcultured organoids having been plated in a culture medium of the disclosure and in accordance with the methods described herein, may undergo media changes approximately every 2-7 days, or as appropriate in order to avoid collapse of the organoid lumen. However, if the organoids have been embedded in an extracellular matrix, it may be possible to restore the lumen of collapsed organoids to an inflated state. Notably, even collapsed organoids that have been in culture for one month, or longer, without subculturing or medium changes may be revived using the disclosed culture media.

In certain embodiments it may be desirable to use different media at different stages of culture. For example it may be desirable to initiate the cultures in one type of medium, for example in one of Medium A, Medium B, Medium C, or Medium D. After a certain number of passages or the passage of a certain amount of time, it may desirable to use a different type of medium, for example a different one of Medium A, Medium B, Medium C, or Medium D. In another embodiment it may be desirable to cycle between one type of medium such as Medium A, Medium B, Medium C, or Medium D and a different type of medium, such as a different one of Medium A, Medium B, Medium C, or Medium D during different stages of culture.

Referring to hepatic organoids in particular, the initiation of hepatic organoids may be dependent on Lgr5+ cells and/or other positive marker expression representing stem/progenitor cells. However, the epithelial stem cell marker Lgr5 may generally not be active under conditions of homeostasis. Rather, the epithelial stem cell marker Lgr5 may typically be activated upon tissues becoming subject to obstructive, mechanical or toxic injury. Accordingly, epithelial organoids are oftentimes obtained from liver tissue that was subject to injury. In one embodiment of the present disclosure, the epithelial ducts, epithelial duct fragments and/or epithelial stem cells isolated therefrom are obtained from uninjured tissue. As used herein, the term "uninjured tissue" refers to tissue that has not been subjected to obstructive, mechanical and/or toxic injury.

In one embodiment of the present disclosure, epithelial organoids are derived from one or more freshly isolated epithelial ducts, epithelial duct fragments and/or epithelial stem/progenitor cells or epithelial fragments comprising epithelial stem/progenitor cells from mouse tissue obtained from male or female mice approximately 1 year old or younger that have not been subject to prior injury.

In one embodiment, the epithelial organoids obtained by the methods described herein are further subjected to maturation and/or differentiation conditions. As used herein, the term "maturation and/or differentiation conditions" refers to culture conditions which promote the maturation and differentiation of the epithelial organoids into mature cell types. Various maturation and differentiation conditions are known in the art, and can be specifically selected depending on the mature cell type of interest. In one embodiment, hepatic and/or pancreatic organoids obtained by the methods described herein are further subjected to maturation and/or differentiation conditions.

Organoids and Uses Thereof

The present disclosure provides epithelial organoids obtained by the methods described herein. In one embodiment, the organoids are hepatic, pancreatic or intestinal organoids.

Organoids obtained by the methods described herein are optionally human organoids. Non-human animal organoids are also contemplated herein.

Epithelial organoids formed using the methods described herein may express one or more gene or protein markers characteristic of the epithelial tissue from which the organoids derive. For example, hepatic organoids may express one or more of the following genes: Lgr5, Axin2, Hnf4a, Epcam, ZO1, Krt19 and Sox9. As another example, pancreatic organoids may express one or more of the following genes: Lgr5, Sox9, Pdx1, Krt7, Muc1 and Car2. As another example, intestinal organoids may express one or more of the following genes: Lgr5, Lyz, Vil1, ChgA and Muc2.

The self-renewal of hepatic organoids formed using the methods and media described herein may be primarily driven by Axin2 rather than Lgr5, offering a more physiologically-relevant culture system for hepatic homeostasis (Wang et al., 2015 Nature).

The disclosure also provides pharmaceutical compositions comprising an organoid described herein and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e. topical), transmucosal, and rectal administration.

Various uses of epithelial organoids are known in the art.

In particular, the organoids and/or pharmaceutical compositions of the present disclosure are useful for treating a disorder, condition or disease or for regenerative medicine in a subject.

In one embodiment, the organoids of the present disclosure are used in a method for treating a disorder, condition or disease or for regenerative medicine, the method comprising administering the organoids to a subject in need thereof.

In another embodiment, a method of treating a liver disorder, condition or disease or for regenerative medicine in a subject is provided, where the method comprising administering a liver organoid obtained by the methods described herein to a subject. In one embodiment, the liver disorder, condition or disease is Alagille Syndrome, Wilson Disease, Type 1 Glycogen Storage Disease, Alpha 1 Anti-Trypsin Deficiency, Fibrosis, Cirrhosis, Neonatal/Viral (A, B,C)/Autoimmune/Toxic Hepatitis, Fatty Liver Disease, Tyrosinemia, Sarcoidosis, Lysosomal Acid Lipase Deficiency, Hepatic Tumours, Cystic Disease of the Liver, Biliary Atresia, Galactosemia, Primary Biliary Cholangitis, Porphyria, Reye's Syndrome, Hemochromatosis, Gilbert's Syndrome, Hepatic Steatosis and Gallstones.

In a further embodiment, a method of treating a pancreatic disorder, condition or disease or for regenerative medicine in a subject is provided, where the method comprising administering a pancreatic organoid obtained by the methods described herein to a subject. In one embodiment, the pancreatic disorder, condition or disease is Acute/Chronic/Hereditary Pancreatitis, Pancreatic Tumours, Diabetes Mellitus, Cystic Fibrosis, Exocrine Pancreatic Insufficiency, Congenital Malformations (Pancreas Divisum, Annular Pancreas), Zollinger-Ellison Syndrome and Pancreatic Cysts/Pseudocysts.

In a further embodiment, a method of treating an intestinal disorder, condition or disease or for regenerative medicine in a subject is provided, where the method comprising administering an intestinal organoid obtained by the methods described herein to a subject. In one embodiment, the intestinal disorder, condition or disease is Cystic Fibrosis, Ulcerative Colitis, Crohn's Disease, Colorectal Cancer, Colonic Polyps, Irritable Bowel Syndrome, Coeliac Disease, Fecal Incontinence, Lactose Intolerance, Diverticulosis/Diverticulitis, Acid Reflux, Diarrhea, Peptic Ulcers, Short Bowel Syndrome, Curling's Ulcer, Blind Loop Syndrome, Milroy Disease, Whipple's Disease, Carcinoid Syndromes, Hirschsrung's Disease and Anal Cancer.

In another embodiment, an effective amount of an organoid disclosed herein is used in the preparation of a medicament for treating a disorder, condition or disease or for regenerative medicine. An effective amount of an organoid of the disclosure relates generally to the amount needed to achieve a therapeutic objective.

As used herein, the term "subject" includes all members of the animal kingdom, in one embodiment the subject is a mammal. In a further embodiment the subject is a human being.

As used herein, "treating a disorder, condition or disease" includes, but is not limited to, reversing, alleviating or inhibiting the progression of the disorder, condition or disease or symptoms or conditions associated with the disorder, condition or disease.

The organoids described herein may also be useful in methods of: conducting drug discovery screens; assaying toxicity; researching embryology, cell lineages, and differentiation pathways; studying gene expression including recombinant gene expression; researching mechanisms involved in injury and repair; researching inflammatory and infectious diseases; and studying pathogenic mechanisms of cell transformation and etiology of cancer The following non-limiting examples are illustrative of the present disclosure:

Example 1—Digesting Organs or Portions Thereof

Whole organs comprising epithelia from male and female mice (i.e. C57BL/6) were dissected and cut into approximately 1-3 mm$^3$ pieces of tissue. The ~1-3 mm$^3$ pieces of epithelial tissue were bathed in approximately 25 mL of ice-cold DMEM/F-12. The volume of ice-cold DMEM/F-12 containing the epithelial fragments was transferred to a 50 mL Falcon tube using a 25 mL serological pipette. The pieces of epithelial tissue were permitted to settle under the force of gravity for approximately 2 minutes, and the supernatant was discarded. The pellet of pieces of epithelial tissue was subsequently contacted with 5 mL of an Enzyme Digestion Cocktail comprising Dispase (0.0125% (w/v)) and a Collagenase (0.0125% (w/v)). The pieces of epithelial tissue were incubated in the Enzyme Digestion Cocktail in a 37° C. water bath for 20 minutes. After the 20 minute incubation, the solution was vigorously pipetted approximately 7 times using a 10 mL serological pipette, and the agitated, digested pieces of epithelial tissue were permitted to settle under the force of gravity for approximately 1 minute. The first supernatant was discarded.

Figure 7:
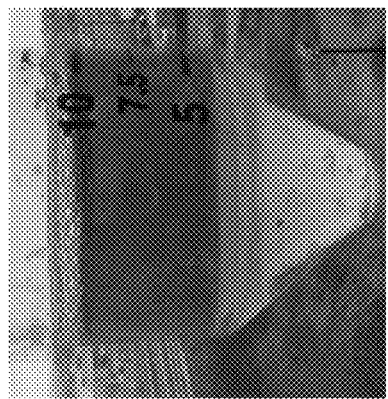
FIG. 7 shows repeated digestion with a buffer comprising digestive enzyme(s). (a) Epithelial tissue may be digested in the presence of a buffer comprising digestive enzyme(s). If digestion is incomplete, the supernatant may be withdrawn and saved, with the pellet subject to a further one or more round of digestion. (b) An exemplary photograph of the appearance of epithelial ducts and/or epithelial duct fragments following digestion of epithelial tissue in a buffer comprising digestive enzyme(s).
Figure 7:
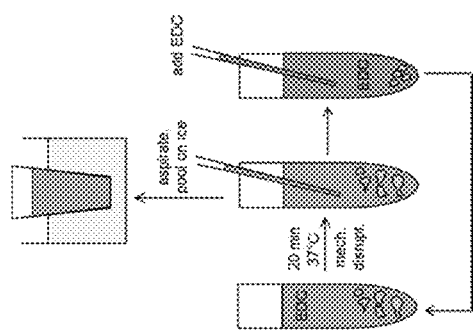

Repeated cycles of digestion, as described above, were performed in order to yield epithelial ducts and/or epithelial duct fragments from the pieces of epithelial tissue (FIG. 7a). As early as after the second cycle of digestion, epithelial ducts and/or epithelial duct fragments may be present in the supernatant (FIG. 7b). Once epithelial ducts and/or epithelial duct fragments became present in the supernatant, the supernatant was removed and placed in an appropriate tube. The supernatant from successive cycles of digestion of the remaining pieces of epithelial tissue were pooled.

5-7 digestion cycles of each 20 minutes digested substantially all of the pieces of epithelial tissue into epithelial ducts and/or epithelial duct fragments.

Example 2—Yield After Digesting Organs or Portions Thereof

The set aside pooled supernatant was subjected to filtration (as shown in FIG. 4) in order to isolate epithelial ducts and/or epithelial duct fragments from single cells, such as terminally differentiated cells and debris. The pooled supernatant was passed through a 40 μm filter and the flow through was discarded. The filtrant on the filter surface was collected by carefully reversing the filter surface and placing it over top of a 50 mL Falcon tube. Approximately 10 mL of ice-cold Advanced DMEM/F-12 was passed over the under surface of the filter surface causing the filtrant to wash away from the filter surface and collect inside the tube. The washing was repeated until all or substantially all filtrant was washed off the filter. Collection may be aided by scraping the filter. The tube was centrifuged at 300×g for 5 minutes to pellet the epithelial ducts and/or epithelial duct fragments, and the supernatant was discarded. Optionally, the 10 mL suspension of filtrant, comprising epithelial ducts and/or epithelial duct fragments were aliquoted into 3-10 tubes prior to centrifugation.

Example 3—Pre-Clearing the Yield After Digesting Organs or Portions Thereof

The set aside pooled supernatant was subjected to filtration (as shown in FIG. 4) in order to isolate epithelial ducts and/or epithelial duct fragments from single cells, such as terminally differentiated cells and debris. The pooled supernatant was first passed through a 70 µm filter and the flow through was retained. The filtrant, comprising debris such as undigested tissue and ducts was discarded (or alternatively it may be exposed to further digestion and/or embedded in an extracellular matrix as outlined in Examples 4 or 5). The portion of the pooled supernatant that passed through the 70 µm filter was then passed through a 40 µm filter as described in Example 2. The filtrant on the filter surface was collected by carefully reversing the filter surface and placing it over top of a 50 mL Falcon tube. Approximately 10 mL of ice-cold Advanced DMEM/F-12 was passed over the under surface of the filter surface causing the filtrant to wash away from the filter surface and collect inside the tube. The washing was repeated until all or substantially all filtrant was washed off the filter. Collection was aided by scraping the filter. The tube was centrifuged at 300×g for 5 minutes to pellet the epithelial ducts and/or epithelial duct fragments, and the supernatant was discarded. Optionally, the 10 mL suspension of filtrate, comprising epithelial ducts and/or epithelial duct fragments was equally aliquoted into 3-10 tubes prior to centrifugation.

Example 4—Plating the Epithelial Ducts and/or Epithelial duct Fragments in Matrigel™ Domes The pelleted epithelial ducts and/or epithelial duct fragments were resuspended in an appropriate volume of thawed Matrigel™. Approximately 30 µL to 300 µL of Matrigel™ was used to resuspend the epithelial ducts and/or epithelial duct fragments obtained from one mouse organ if they were not equally aliquoted into 3-10 tubes. Otherwise, a volume of about 10 µL to 30 µL of Matrigel™ was used to resuspend the epithelial ducts and/or epithelial duct fragments having been aliquoted into each of the 3-10 tubes.

It was also possible to dilute the mixture of Matrigel™ and epithelial material to contain up to 90% (v/v) cell culture medium without compromising the stability of a subsequently plated Matrigel™ dome.

The suspension of epithelial ducts and/or duct fragments were deposited as 25-60 µL droplets on a bottom surface of a pre-warmed 24-well plate and allowed to polymerize for 10 minutes at 37° C. into domes. The 8 wells in the center of the 24-well plate were most suitable for depositing the Matrigel™ droplets because they are the least slanted.

While dispensing the suspension of epithelial ducts and/or epithelial duct fragments, the pipette tip was gradually moved upwardly to avoid adhesion of the epithelial ducts and/or epithelial duct fragments to the outside of the pipette tip and to evenly distribute the epithelial ducts and/or epithelial duct fragments within the dome.

Example 5—Plating the Epithelial Ducts and/or Epithelial duct Fragments in Suspension with Reduced Support of an Extracellular Matrix Epithelial ducts and/or epithelial duct fragments were grown in suspension with reduced support from the extracellular matrix. Epithelial ducts and/or epithelial duct fragments obtained as outlined in Example 2 or Example 3 were mixed with culture medium. This mixture was chilled to 4° C. when in combination with reduced extracellular matrix (e.g. Matrigel™ at concentrations between 0.1% and 50% (v/v)). Using low-adherence plates (e.g. 12-well plates), the epithelial material suspended in cell culture medium (and reduced Matrigel™ concentration) was added to each well and maintained at 37° C. under rotation at 70-80 rpm.

Example 6—Culture of Epithelial Ducts and/or Epithelial Fragments in Culture Medium Without disturbing the polymerized Matrigel™ dome, approximately 750 µL of culture medium was added against a sidewall of the well containing the one or more Matrigel™ domes. Any well that did not contain a Matrigel™ dome received 750 µL of a sterile liquid such as PBS, culture medium, or the like.

An image of each Matrigel™ dome was taken on day 0, and regularly thereafter (FIG. 1). The medium was changed every 2-7 days for up to one week, by carefully removing the medium from each well. A 750 µL volume of a pre-warmed (ie. 20-37° C.) culture medium was added to each well.

Example 7—Culture of Epithelial Ducts or Epithelial Fragments in Medium A

The methods described in Example 6 were used for forming and expanding hepatic organoids using a medium comprising DMEM/F-12, and about: 15 mM HEPES, 1.2 g/L sodium bicarbonate, 0.5 mM L-Alanyl-L-glutamine, 61.5 µg/mL Rh insulin, 0.012 µg/mL progesterone, 64 µg/mL putrescine, 0.0104 µg/mL sodium selenite, 80 µg/mL human apo-transferrin, 0.02 µg/mL corticosterone, 15 µg/mL D-(+)-Galactose, and 2600 µg/mL BSA.

Such medium supported the formation and expansion of hepatic organoids for about 5 passages.

Example 8—Culture of Epithelial Ducts or Epithelial Fragments in Medium B

The methods described in Example 6 were used for forming and expanding epithelial organoids using culture Medium A of Example 7 to which 0.016 µg/mL R-Spondin-1 and/or 3.75 µM CHIR 99021 was added.

In the presence of both R-Spondin-1 and CHIR 99021, the formation and expansion of epithelial organoids was supported for about 20 or more passages. In the presence of only one of R-Spondin-1 or CHIR 99021 the formation and expansion of epithelial organoids was supported for about 10 or more passages.

Example 9—Culture of Epithelial Ducts or Epithelial Fragments in Medium C

The methods described in Example 6 were used for forming and expanding epithelial organoids using a culture medium of Example 8, to which 0.05 µg/mL EGF was added.

Such medium supported the formation and expansion of epithelial organoids for about 40 or more passages.

Example 10—Culture of Epithelial Ducts or Epithelial Fragments in Medium D

The methods described in Example 6 were used for forming and expanding epithelial organoids using culture medium C of Example 9, to which 0.016 µg/mL Noggin, and 0.1 µM LDN 193189 was added.

Such medium supported the formation and expansion of epithelial organoids for about 50 or more passages.

Example 11—Formation of Hepatic Organoids and Expression of Markers Thereof

Hepatic organoids were formed and expanded when a liver was processed in accordance with Examples 1 and 2, and optionally Example 3, plated in accordance with Example 4 or 5, and cultured in the presence of a medium described in Examples 7-10. In one example, the liver was processed in accordance with Examples 1, 4 and 7.

Figure 8:
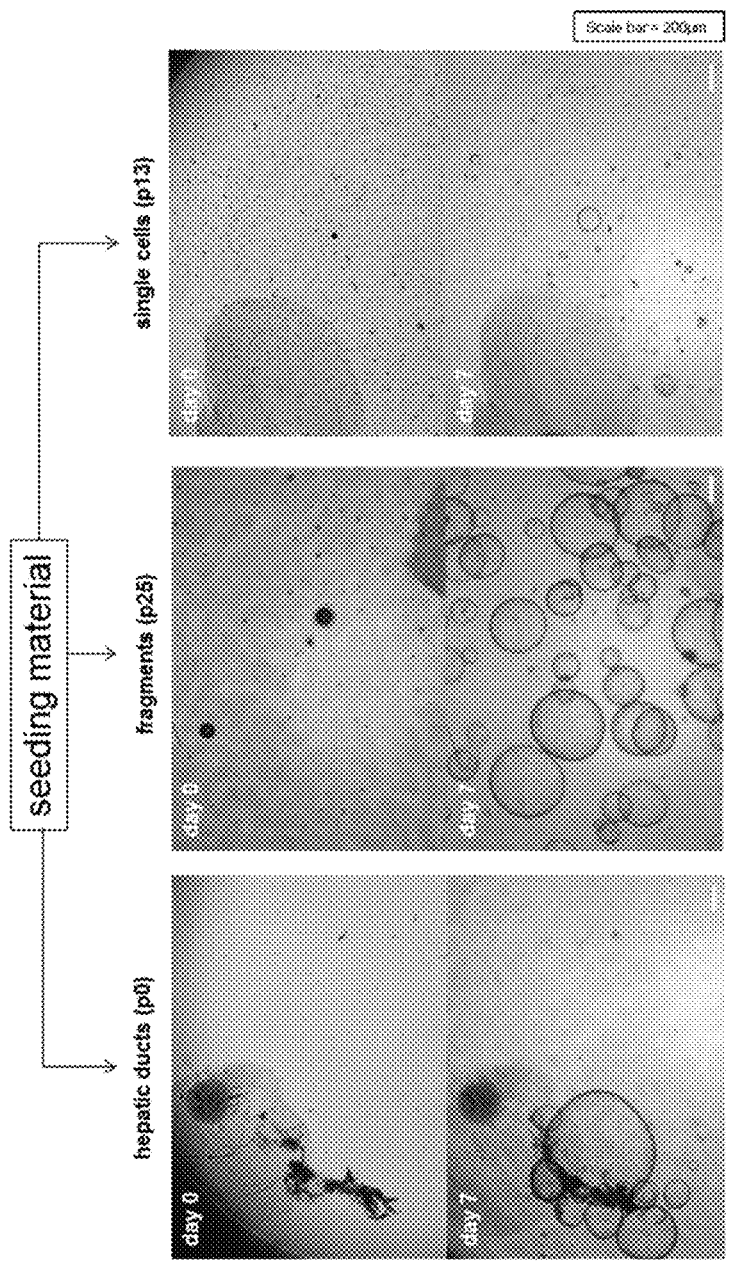
FIG. 8 shows that hepatic organoids may be maintained and expanded regardless if the material plated is hepatic ducts and/or hepatic duct fragments, mechanically disrupted and/or enzymatically digested hepatic organoids, or single epithelial stem and/or progenitor cells contained within hepatic ducts and/or hepatic duct fragments.
Figure 9:
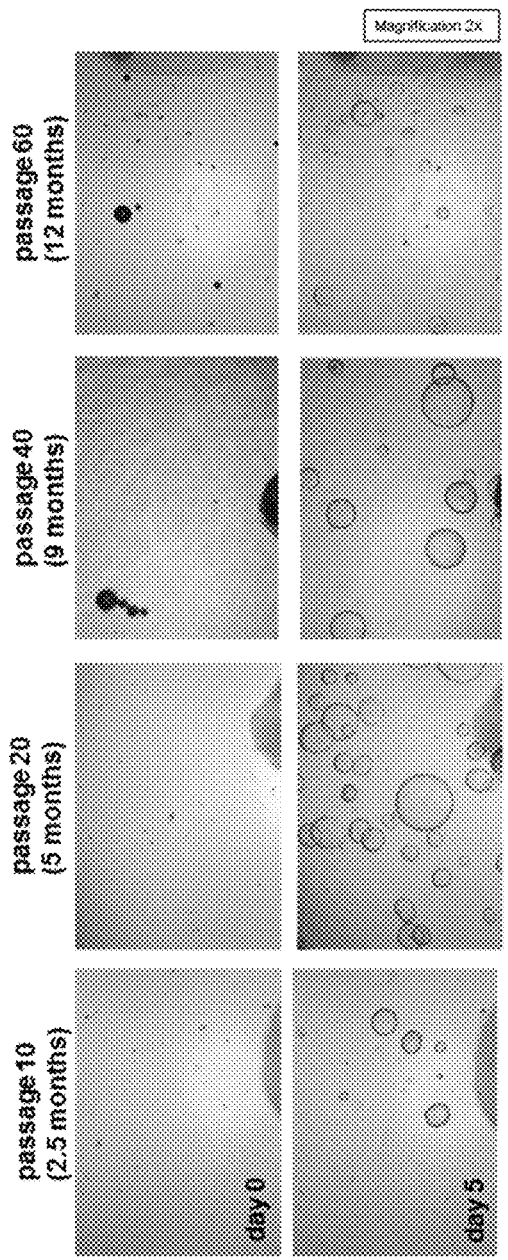
FIG. 9 shows that hepatic organoids may be subcultured and expanded long-term.

The formation and expansion of hepatic organoids occurred regardless of plating hepatic ducts, hepatic duct fragments, single epithelial stem and/or progenitor cells, or mechanically disrupted or enzymatically digested hepatic organoids (FIG. 8). Once formed, hepatic organoids were maintained and expanded long-term through passaging (FIG. 9).

Figure 10:
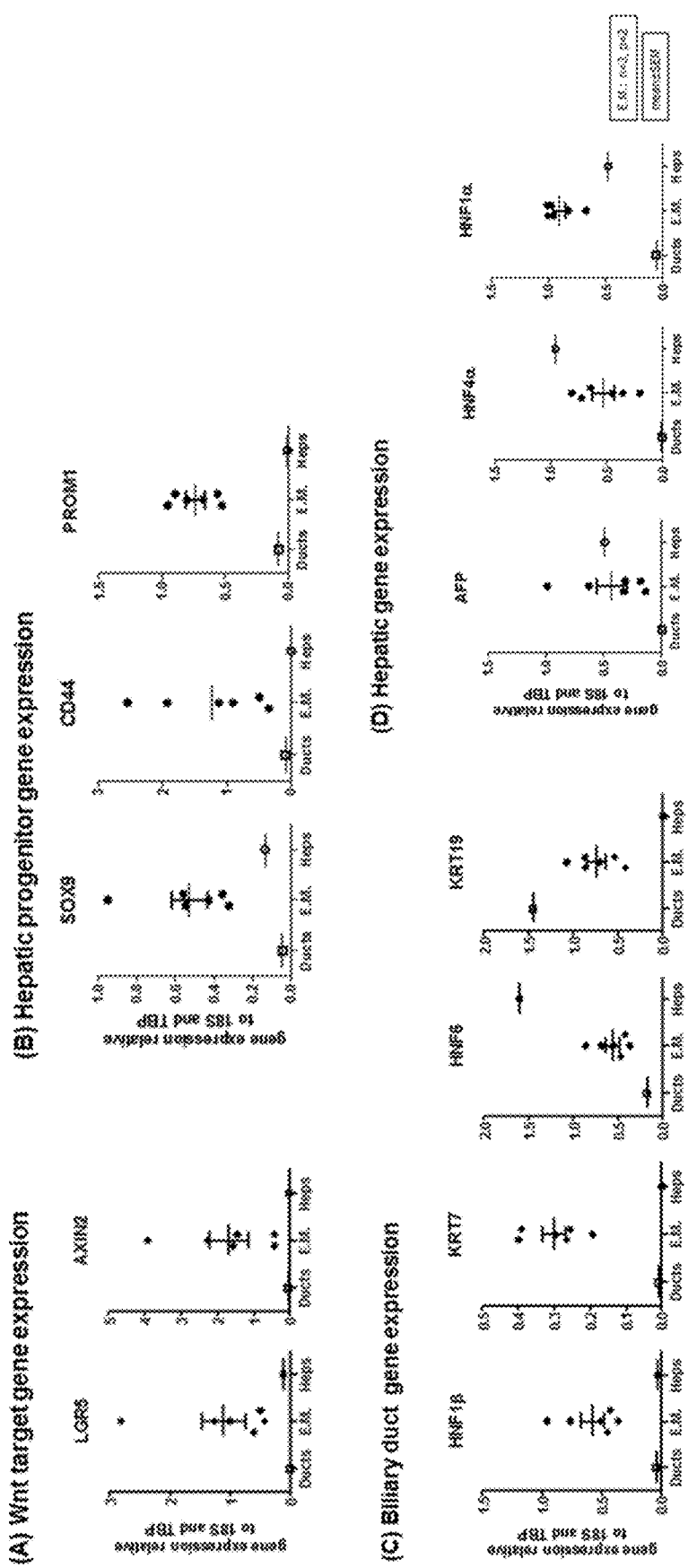
FIG. 10 shows gene expression profiling by RT-PCR of liver organoids, hepatic ducts and/or duct fragments, and primary mouse hepatocytes. (a) Assessment of Wnt target gene expression. (b) Assessment of hepatic progenitor gene expression. (c) Assessment of biliary duct gene expression. (d) Assessment of hepatic gene expression.
Figure 11:
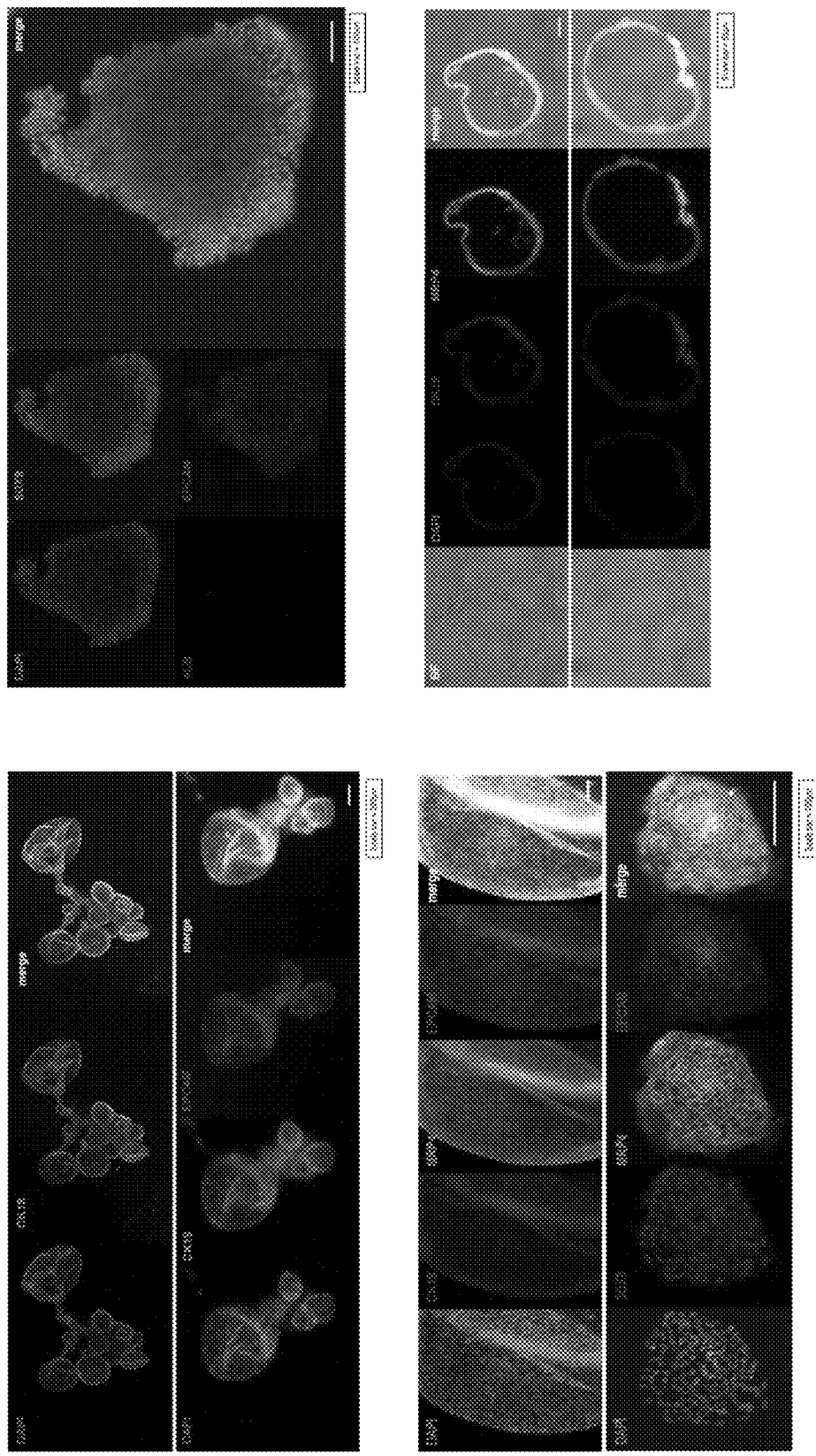
FIG. 11 shows protein synthesis of liver organoids using immunocytochemistry.

Formed and expanded hepatic organoids exhibited a hepatobiliary gene expression, as shown in FIG. 10. Further, hepatic organoids formed and expanded in accordance with the methods and medium disclosed herein synthesize hepatic and ductal proteins (FIG. 11).

Example 12—Formation of Pancreatic Organoids and Expression of Markers Thereof

Pancreatic organoids were formed and expanded when a pancreas was processed in accordance with Examples 1 and 2, and optionally Example 3, plated in accordance with Example 4 or 5, and cultured in the presence of a medium described in Examples 7-10. In one example, the pancreas was processed in accordance with Examples 1, 4 and 7.

Figure 12:
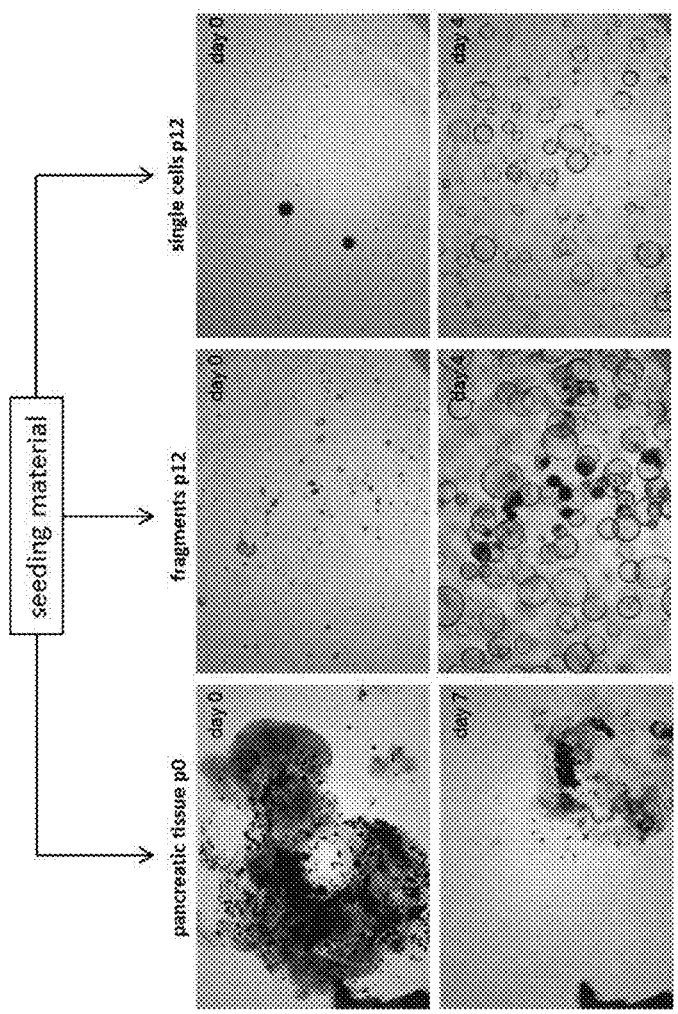
FIG. 12 shows that pancreatic organoids may be maintained and expanded regardless if the material plated is pancreatic ducts and/or pancreatic duct fragments, mechanically disrupted and/or enzymatically digested pancreatic organoids, or single epithelial stem and/or progenitor cells contained within pancreatic ducts and/or pancreatic duct fragments.
Figure 13:
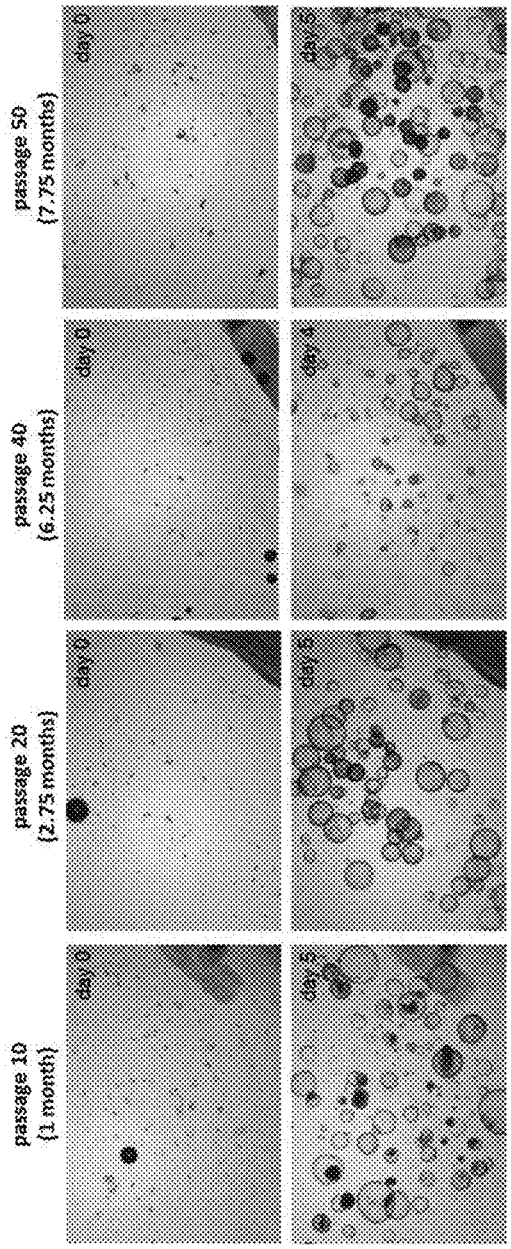
FIG. 13 shows that pancreatic organoids may be subcultured and expanded long-term.

The formation and expansion of pancreatic organoids occurred regardless of plating pancreatic ducts, pancreatic duct fragments, single epithelial stem and/or progenitor cells, or mechanically disrupted or enzymatically digested pancreatic organoids (FIG. 12). Once formed, pancreatic organoids were maintained and expanded long-term through passaging (FIG. 13).

Figure 14:
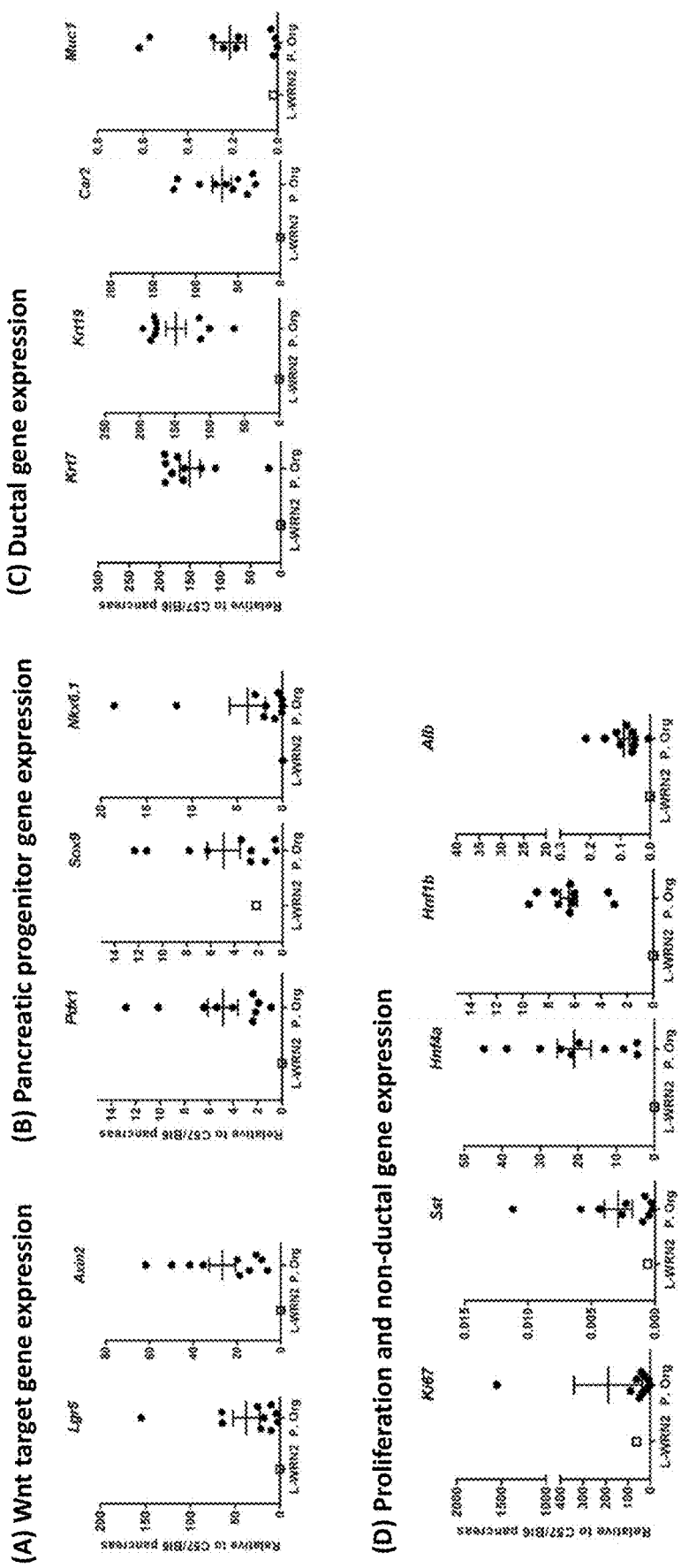
FIG. 14 shows gene expression profiling by RT-PCR of pancreatic organoids, mouse fibroblasts, and hepatic organoids. (a) Assessment of Wnt target gene expression. (b) Assessment of pancreatic progenitor gene expression. (c) Assessment of ductal gene expression. (d) Assessment of proliferation and non-ductal gene expression.
Figure 15:
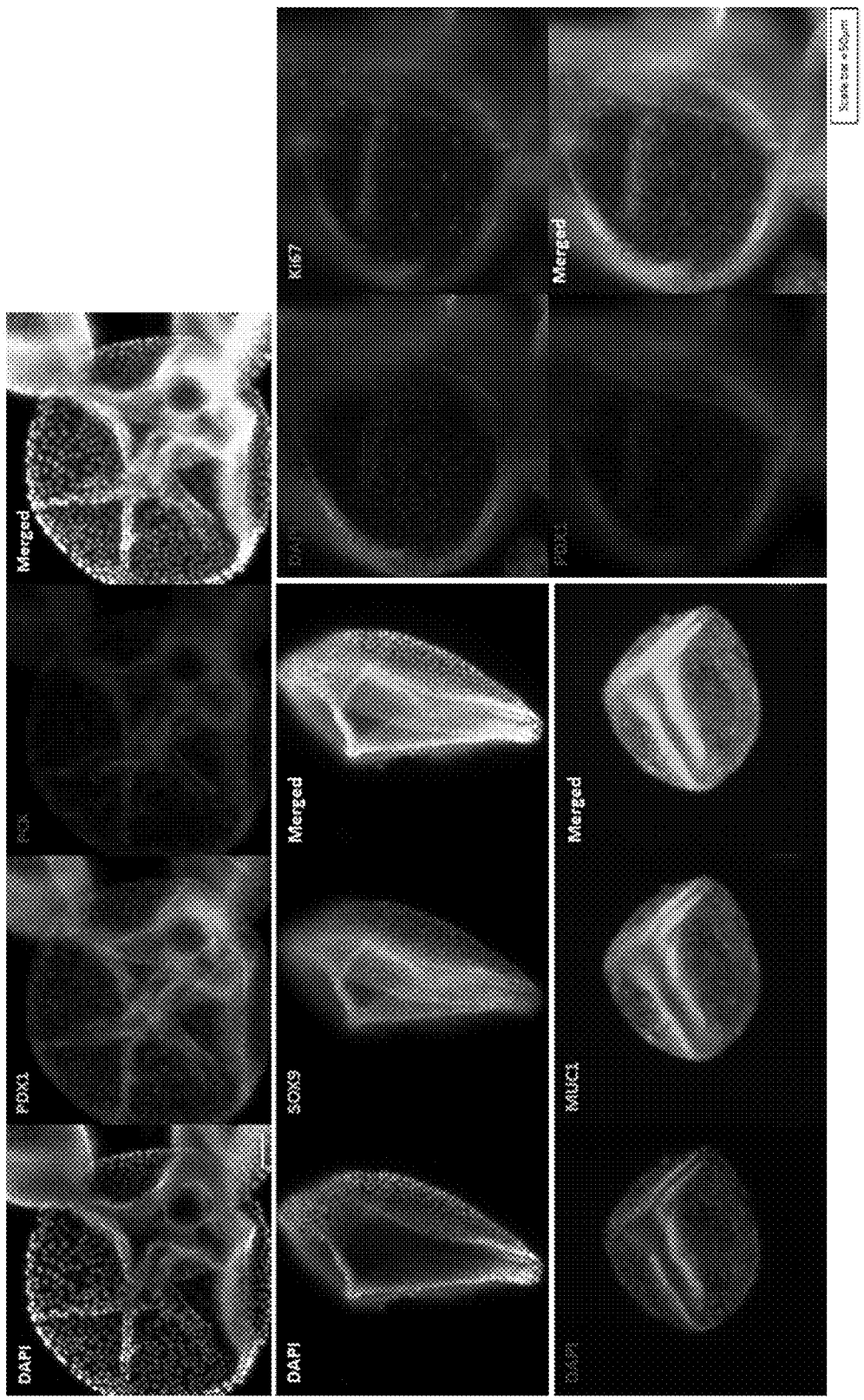
FIG. 15 shows protein synthesis of pancreatic organoids using immunocytochemistry.

Formed and expanded pancreatic organoids exhibit expression of pancreatic ductal genes, as shown in FIG. 14. Further, pancreatic organoids formed and expanded in accordance with the methods and medium disclosed herein synthesize pancreatic ductal proteins (FIG. 15).

Figure 16:
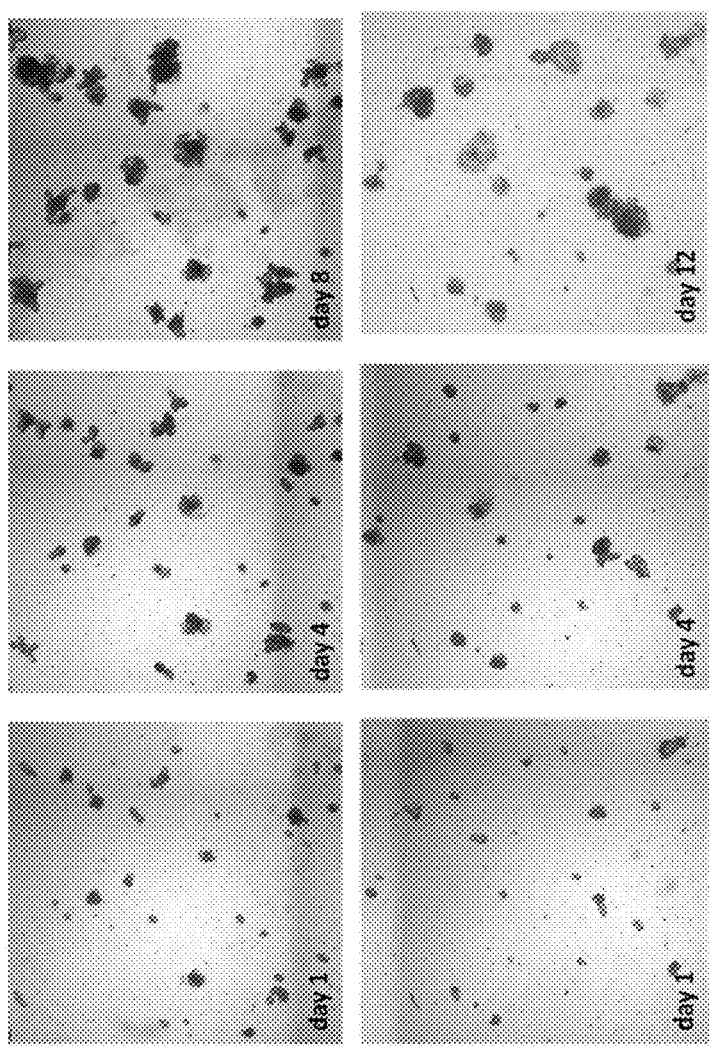
FIG. 16 shows that intestinal organoids may be maintained and expanded from intestinal crypts.

Example 13—Formation of Small Intestinal and Colonic Organoids and Expression of Markers Thereof Small intestinal and colonic organoids were formed and expanded when a small intestine or colon was processed in accordance with Examples 1 and 2, and optionally Example 3, plated in accordance with Example 4 or 5, and cultured in the presence of a medium described in Examples 7 or 8 (FIG. 16). In one example, the intestine was processed in accordance with Examples 1, 4 and 7.

Figure 17:
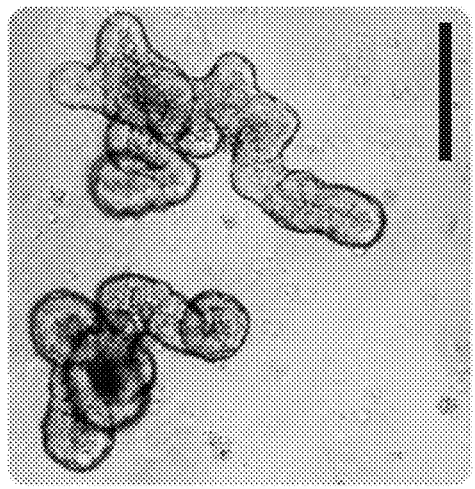
FIG. 17 shows that intestinal organoids can be expanded from crypts or single cells.
Figure 17:
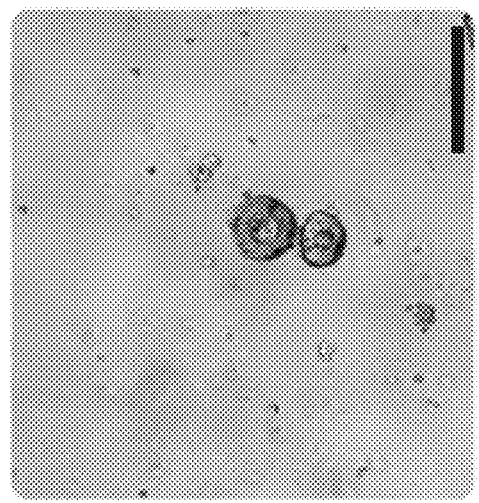
Figure 17:
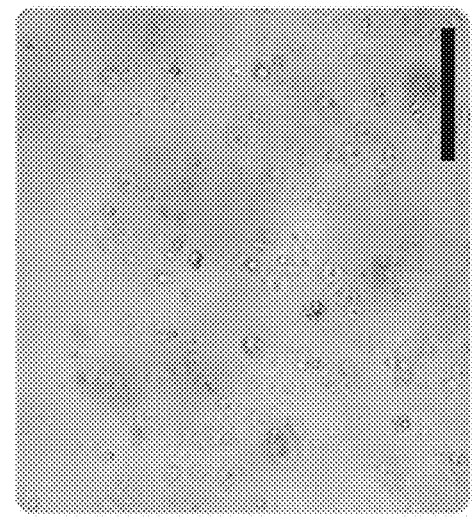
Figure 17:
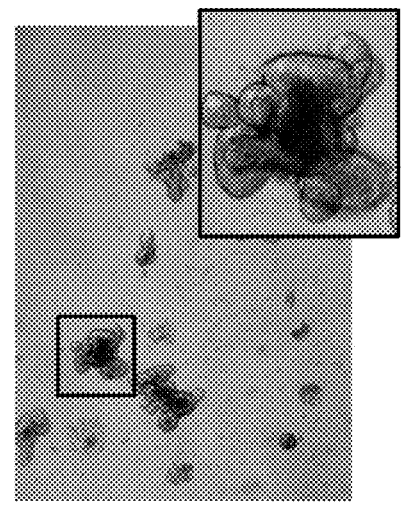
Figure 17:
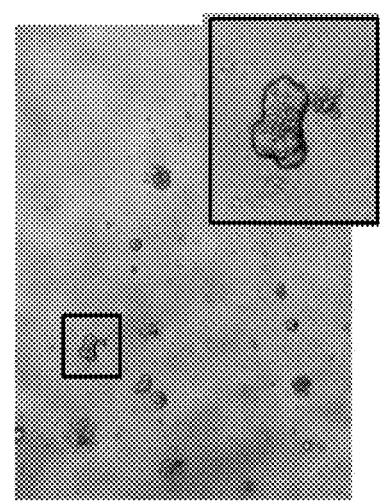
Figure 17:
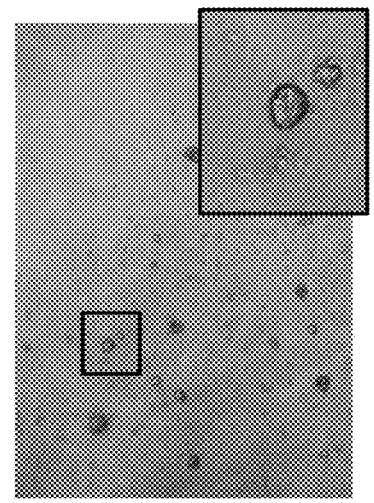

The formation and expansion of intestinal organoids occurred regardless of plating intestinal crypts, intestinal crypt fragments, single epithelial stem and/or progenitor cells, or mechanically disrupted or enzymatically digested intestinal organoids (FIG. 17).

Figure 18:
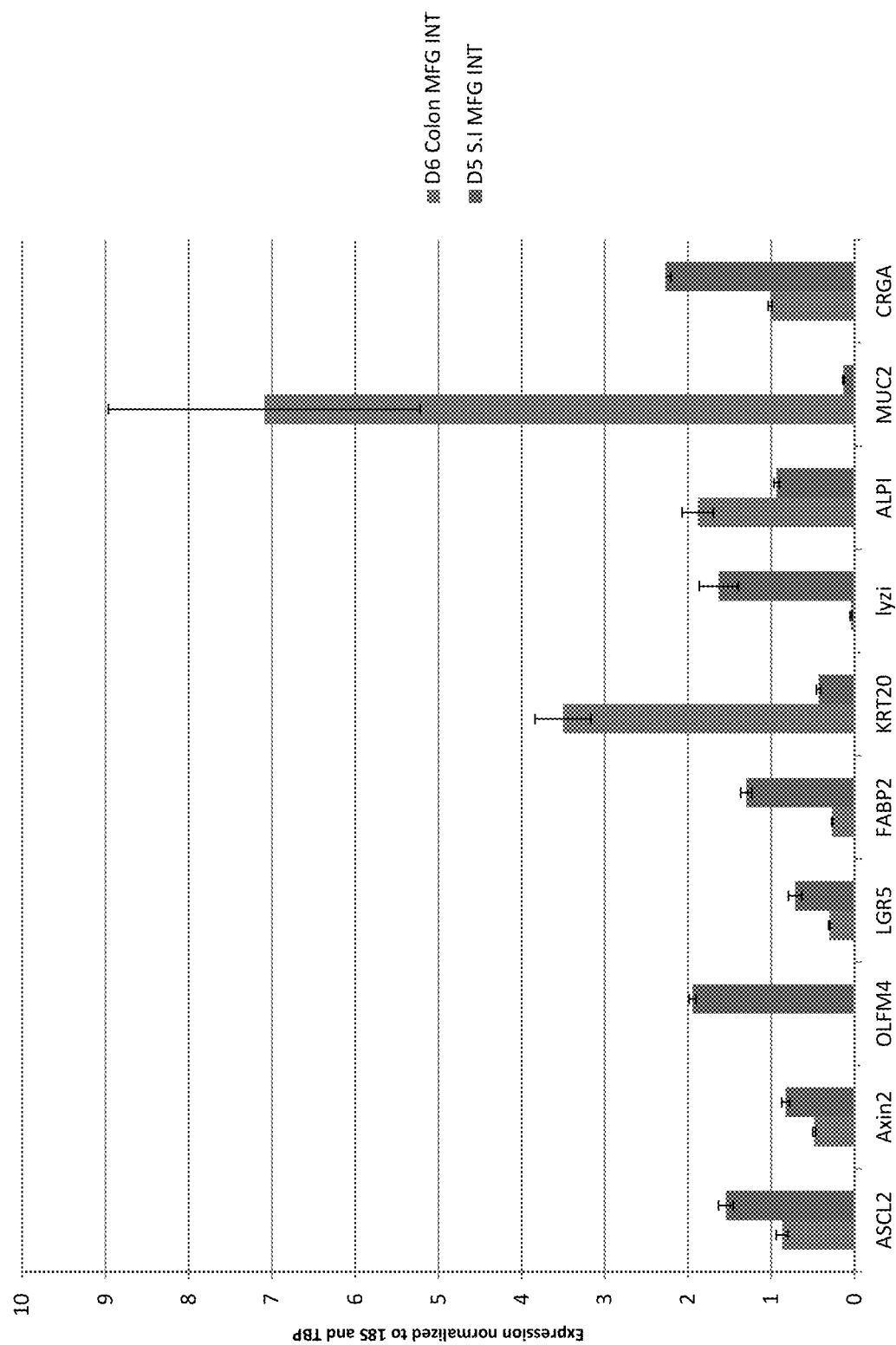
FIG. 18 shows gene expression of intestinal and colonic organoids.
Figure 19:
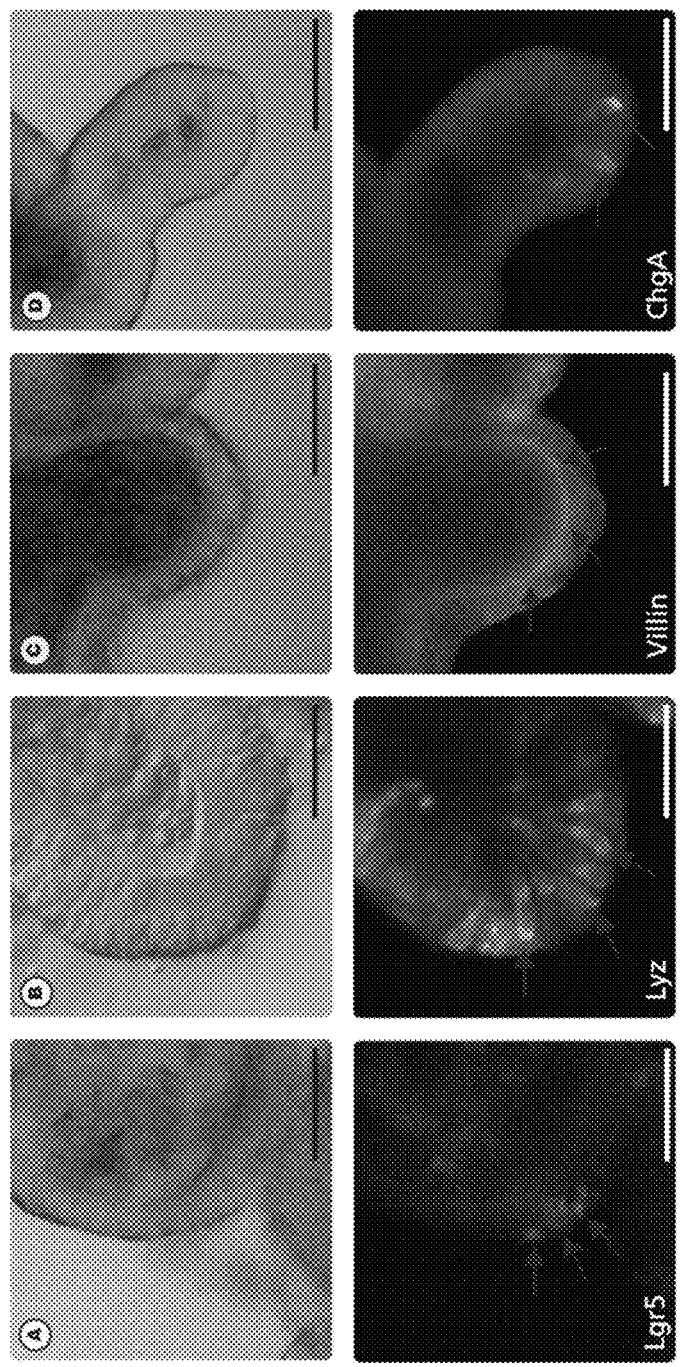
FIG. 19 shows protein synthesis of intestinal markers in small intestine organoids. (a) Lgr5—Stem cell marker, R-spondin receptor, (b) Lysozyme—Paneth cells, (c) Villen—Enterocytes, (d) Chromogranin A—Enteroendocrine cells.
Figure 20:
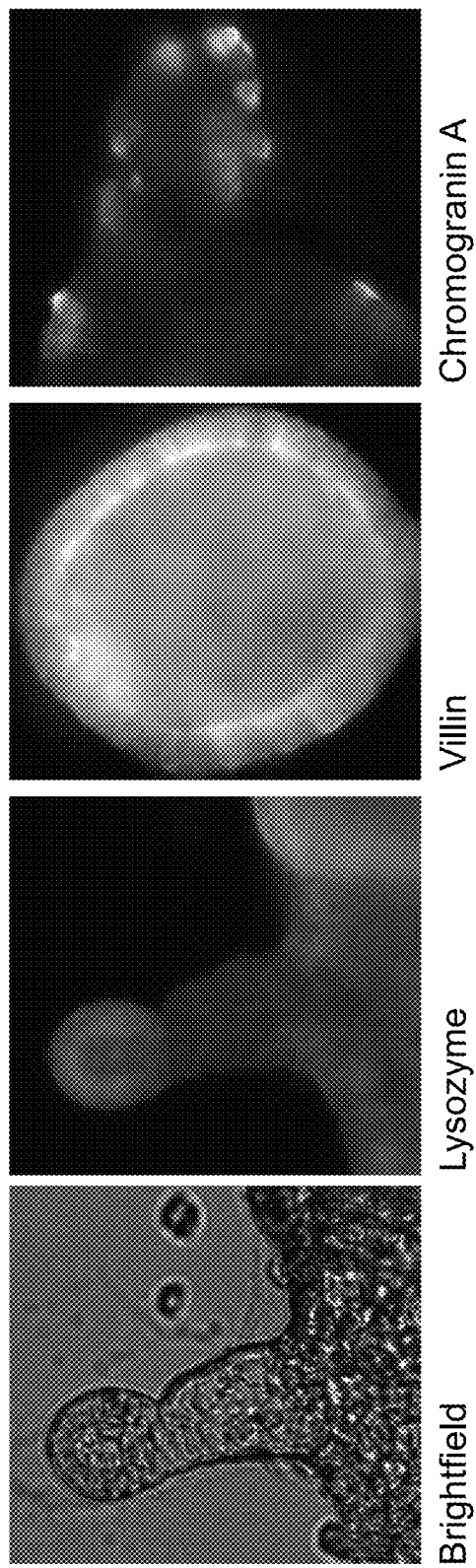
FIG. 20 shows protein synthesis of colonic markers in colon organoids. Lysozyme—Paneth cells; Villin—Enterocytes; Chromogranin A—Enteroendocrine cells.

Formed and expanded intestinal and colonic organoids express intestinal and colonic markers, as shown in FIGS. 18-20.

Example 14—Subculturing Organoids Using Mechanical Disruption

The expansion of organoids plated in accordance with Example 4 or 5 was monitored daily using a light microscope to track their growth, and particularly that the lumen of the organoids had not darkened and collapsed.

If cultured within Matrigel™ domes, the culture medium overlying the Matrigel™ domes was aspirated. Approximately 1000 µL of Advanced DMEM/F-12 was forcefully directed toward the center of each Matrigel™ dome. The volume of Advanced DMEM/F-12 was vigorously pipetted up and down 15 times.

If cultured in suspension (i.e. without or with reduced support of an extracellular matrix), the organoid suspension was vigorously pipetted up and down 15 times.

Three 10 µL volumes of the cell suspension were plated as individual volume domes into an empty well of a 6-well plate for counting. A volume of the cell suspension containing approximately 200 clumps was transferred to a tube containing 1 mL of Advanced DMEM/F-12 and centrifuged at 300×g for 5 minutes. Without disturbing the pellet, the supernatant was carefully aspirated. The pellet was resuspended and plated in accordance with either Example 4 or 5. A culture medium was added to each well containing a Matrigel™ dome as described in Example 6, and specifically using a culture medium having the formulation as described in any one of Examples 7 to 10.

Example 15—Subculturing Organoids Using Enzymatic Digestion

The expansion of organoids plated in accordance with Example 4 or 5 was monitored daily using a light microscope to track their growth, and particularly that the lumen of the organoids had not darkened and collapsed.

If cultured within Matrigel™ domes, the culture medium overlying the Matrigel™ domes was aspirated. Approximately 500 µL of cold Advanced DMEM/F-12 was forcefully added to the center of each Matrigel™ dome and allowed to sit for approximately 1 minute. Using a p1000 pipette tip, the Matrigel™ dome was brought into solution by upward and downward pipetting and compaction, and the volume transferred to a fresh tube. The well was rinsed with 500 µL of Advanced DMEM/F-12 and this volume was pooled with the contents of the fresh tube.

If cultured in suspension (i.e. without or with reduced support of an extracellular matrix), the organoid suspension was transferred to a fresh tube. The well was rinsed with 500 µL of Advanced DMEM/F-12 and this volume was pooled with the contents of the fresh tube.

The contents of the fresh tube were vigorously pipetted 15 times and centrifuged at 300×g for 5 minutes, the supernatant was carefully removed and discarded. The pellet was contacted with 3 mL of Single Cell Dissociation Buffer and incubated in a 37° C. water bath for 10-20 minutes. After the incubation period, 3 mL of Advanced DMEM/F-12 was added to the tube and the number of cells in the suspension was determined using a hemocytometer. The volume containing approximately 1000-8000 live cells was transferred to a 15 mL Falcon tube and centrifuged at 300×g for 5 minutes. The pellet was resuspended and plated in accordance with either Example 4 or 5. A culture medium was added to each well containing a Matrigel™ dome as described in Example 6, and specifically using a culture medium having the formulation as described in any one of Examples 7 to 10.

Example 16—Cryopreservation and Recovery of Epithelial Organoids

Epithelial organoids were cryopreserved in liquid nitrogen for at least one year. Organoids were harvested as outlined in Example 14 or 15 and resuspended in cryopreservation medium containing up to 10% DMSO. The non-DMSO fraction of the cryopreservation medium comprised any one of the media described in Examples 7-10, a commercial basal medium or PBS. Using controlled freezing methods, vials of cryopreservation medium containing epithelial organoids or organoid fragments were first frozen to −80° C. and then transferred to liquid nitrogen for long-term storage. To thaw, vials were removed from liquid nitrogen and placed in a 37° C. water bath. The contents were added drop-wise to a medium of Examples 7-10 and centrifuged at 300×g for 5 minutes. Supplementation of the recovery medium with BSA increased the number of organoids or organoids fragments recovered. The supernatant was removed and the pelleted epithelial material was resuspended and plated as described in Example 4 or 5.

TABLE 1

Selected components of culture media free of a FGF and/or nicotinamide for forming and expanding epithelial organoids.

| Example | A | B | B | C | C | D |
|---|---|---|---|---|---|---|
| EGF | | | | x | x | x |
| Noggin | | | | | | x |
| LDN 193189 | | | | | | x |
| CHIR | | | x | x | | x | x |
| R-spo1 | | x | x | x | x | x |
| Passage Number | P = 5+ | P = 10+ | P = 20+ | P = 30+ | P = 50+ | |
| Split Ratios | 1:1 | 1:4 to 1:8 | 1:4 to 1:8 | 1:4 to 1:8 | 1:4 to 1:70 | |

"x" denotes the presence of the corresponding factor.

The invention claimed is:

1. A method for obtaining an epithelial organoid, the method comprising culturing one or more epithelial ducts, epithelial duct fragments and/or epithelial stem or progenitor cells isolated therefrom in the presence of a basal medium and a wnt agonist, wherein the medium is free from an inhibitor of BMP signaling, and wherein the medium is capable of supporting the organoids for 5 or more passages.

2. The method of claim 1, wherein the Wnt agonist is selected from one or more of CHIR99021, Wnt, Wnt3a, Norrin, R-Spondin1, R-Spondin 2, R-Spondin 3, R-Spondin 4 and a GSK inhibitor.

3. The method of claim 1, wherein the medium comprises one or more members of the EGF family.

4. The method of claim 1, wherein the medium comprises a B27 component and/or a N2 component and/or N-Acetylcysteine.

5. The method of claim 1, wherein the epithelial stem or progenitor cells are hepatic epithelial stem cells, pancreatic epithelial stem cells or intestinal epithelial stem cells.

6. The method of claim 1, wherein the medium is effective for long-term culture of the epithelial organoid, wherein the long-term culture is about 50 or more passages.

7. The method of claim 1, further comprising culturing the one or more epithelial ducts, epithelial duct fragments and/or epithelial stem or progenitor cells:
   (i) in contact with an extracellular matrix or
   (ii) in contact with reduced support from an extracellular matrix or
   (iii) in suspension.

8. The method of claim 1, wherein the epithelial ducts, epithelial duct fragments and/or epithelial stem or progenitor cells isolated therefrom are obtained from uninjured tissue.

9. The method of claim 1, wherein the method further comprises subjecting the epithelial organoid to maturation and/or differentiation conditions.

10. A method for obtaining an epithelial organoid, the method comprising:
   isolating an organ comprising epithelial tissue or a portion thereof;
   cutting and disrupting mechanically the isolated organ or the portion thereof to yield one or more pieces of epithelial tissue;
   digesting enzymatically the one or more pieces of epithelial tissue to yield epithelial ducts and/or duct fragments;
   collecting the digested epithelial ducts and/or duct fragments through a cell strainer;
   plating the collected epithelial ducts and/or duct fragments; and
   culturing the plated epithelial ducts and/or duct fragments in the presence of a basal medium and a wnt agonist, wherein the medium is free from an inhibitor of BMP signaling, and wherein the medium is capable of supporting the organoids for 5 or more passages.

11. The method of claim 10, wherein the Wnt agonist is selected from one or more of CHIR99021, Wnt, Wnt3a, Norrin, R-Spondin 1, R-Spondin 2, R-Spondin 3, R-Spondin 4 and a GSK inhibitor.

12. The method of claim 10, wherein the medium comprises one or more members of the EGF family.

13. The method of claim 10, wherein the medium comprises a B27 component, N2 component, and/or N-Acetylcysteine.

14. The method of claim 10, the method further comprising maintaining intactness of a ductal architecture during digestion.

15. The method of claim 10, the method further comprising treating a surface or implement with a surfactant prior to contact with the one or more pieces of epithelial tissue.

16. The method of claim 10, further comprising plating the collected epithelial ducts and/or epithelial duct fragments:

(i) in contact with an extracellular matrix or
(ii) in contact with reduced support from an extracellular matrix or
(iii) in suspension.

17. The method of claim 10, wherein the method further comprises subjecting the epithelial organoid to maturation and/or differentiation conditions.

18. The method of claim 1, further comprising digesting enzymatically one or more pieces of epithelial tissue multiple times to yield the one or more epithelial ducts, epithelial duct fragments and/or epithelial stem or progenitor cells.

* * * * *